United States Patent
Frederick et al.

[11] Patent Number: 6,017,356
[45] Date of Patent: Jan. 25, 2000

[54] METHOD FOR USING A TROCAR FOR PENETRATION AND SKIN INCISION

[75] Inventors: Christopher J. Frederick, West Chester; Richard F. Schwemberger, Cincinnati; William D. Kelly, Mason, all of Ohio; Joseph F. Paraschac, Santa Clara, Calif.; John P. Measamer, Cincinnati, Ohio

[73] Assignee: Ethicon Endo-Surgery Inc., Cincinnati, Ohio

[21] Appl. No.: 08/933,797

[22] Filed: Sep. 19, 1997

[51] Int. Cl.[7] ..................................................... A61B 17/34
[52] U.S. Cl. ........................... 606/185; 604/264; 606/167; 606/170
[58] Field of Search ................................. 606/167, 170, 606/172, 185; 604/164, 264

[56] References Cited

U.S. PATENT DOCUMENTS

| | | | |
|---|---|---|---|
| 4,535,733 | 8/1985 | Honda | 123/90.17 |
| 4,539,976 | 9/1985 | Sharpe | 128/6 |
| 5,314,417 | 5/1994 | Stephens et al. | 604/264 |
| 5,323,765 | 6/1994 | Brown | 128/4 |
| 5,350,393 | 9/1994 | Yoon | 606/185 |
| 5,364,372 | 11/1994 | Danks et al. | 604/264 |
| 5,431,635 | 7/1995 | Yoon | 604/165 |
| 5,571,134 | 11/1996 | Yoon | 606/185 |
| 5,591,190 | 1/1997 | Yoon | 606/185 |
| 5,607,440 | 3/1997 | Danks et al. | 606/185 |
| 5,609,604 | 3/1997 | Schwemberger et al. | 606/185 |

*Primary Examiner*—Michael Buiz
*Assistant Examiner*—Daphna Shai
*Attorney, Agent, or Firm*—Matthew S. Goodwin

[57] ABSTRACT

A method for establishing a surgical port for endoscopic or arthroscopic surgery is disclosed. A trocar is initially provided, and the obturator of the trocar includes a flat cutting blade, a shield that moves proximally and distally from a precock position to an extended position, a precock lever to move the shield proximally to expose the flat cutting blade, and a shield retaining assembly to constrain the shield in the proximal position. "Precocking" the trocar of the present invention moves the shield from the distal position wherein the flat blade is covered, to a proximal position wherein the flat blade is exposed, and the shield is constrained by the shield retaining assembly. Once the flat cutting blade is exposed, the skin of the patient is incised with the flat cutting blade of the obturator. The flat blade of the trocar is inserted into the incision and a penetrating force is applied so that the flat blade penetrates into the internal body cavity of the patient. The obturator assembly is removed from the cannula assembly so that the surgical access port is provided into the internal body cavity of the patient. This method eliminates the need for a separate surgical sharp to initially incise the skin before penetration is effected.

4 Claims, 20 Drawing Sheets

METHOD FOR USING A TROCAR FOR PENETRATION AND SKIN INCISION

BACKGROUND OF THE INVENTION

The present invention relates in general to trocars for use in endoscopic, laparoscopic, and arthroscopic surgery, and in particular, to trocars that employ a moveable shield to establish a surgical port in an internal body cavity.

Trocars are generally assembled from two primary components, a cannula tube and an obturator. The trocar assembly is inserted through the skin to gain access to a body cavity so that endoscopic surgery can be performed. The trocar is placed against the outer skin of a patient, and pushed through the layers of skin, fat, muscle, and fascia until the trocar enters the body cavity. Once the trocar is properly positioned, the surgeon removes the obturator so the cannula can be used as an access port for endoscopic instrumentation.

The trocar and obturator assembly, while of great benefit, could inadvertently penetrate organs or other body structures during insertion. The addition of a moveable shield to envelop the piercing or cutting tip of the trocar was a breakthrough concept. The shield consists of a spring loaded generally tubular member interposed between the piercing or cutting tip and the trocar cannula. In the unbiased state, the shield covers the piercing tip of the obturator. When the distal shielded end of the trocar is pressed against the skin of a patient, the shield retracts to expose the piercing or cutting tip. When the body layers are penetrated, the force on the shield lessens and the shield spring biases the shield distally to envelop the piercing tip. Any further distal motion into the body cavity results in the blunt shield contacting the underlying organs or structures, rather than a cutting or piercing tip. A trocar describing such a shield can be seen in U.S. Pat. No. 4,535,773.

Typically, the piercing or cutting tip of a trocar has been of a conventional pyramidal or conical shape. While the tip is effective in penetrating tissue, the use of a flat, razor blade has been found to offer less trauma to tissue during penetration and is described in U.S. Pat. Nos. 5,314,417 (Stephens et al.) and 5,609,604 (Schwemberger et al.). The flat blade, as described in these patents, is shielded within a tapered bullet shaped shield that offered additional improvements in accordance with the principles of Deniega, as found in U.S. Pat. No. 5,066,288. The combination of a flat blade that produces a diametral slit in tissue with a shield shape that dilates the tissue as it penetrates, was found to reduce the force of penetration, improve the shield response time, and improve healing.

With the flat bladed shielded trocar, new levels of safety and performance were reached. However, there are disadvantages, such as an increased force to penetrate, caused by the need to overcome the shield spring force to expose the piercing tip. It would therefore be desirable to provide a shield with a precock feature that enables the shield to be retracted and locked in an armed position, with the piercing or cutting tip exposed. This precocking action would desirably compress the shield biasing spring, arm the shield in an in a ready to deploy condition, and reduces the force of penetration. A trocar describing such a shield, with a pyramidial tip, is described in U.S. Pat. No. 5,431,635 (Yoon).

While the precocking shield with a pyramidial tip addressed the conventional shield retraction problem, it did not provide the means for the surgeon to make the initial skin incision at the trocar insertion site. This incision is generally made in the skin to reduce the penetration force and requires the use of two surgical instruments to make a trocar insertion, a trocar and a scalpel. The scalpel, or surgical sharp, poses a handling risk to surgical personnel as surgical gloves can be inadvertently cut or nicked during the exchange, exposing the handler to bloodborne diseases. The scalpel is passed back and forth each time a trocar, or surgical access port, is inserted, providing multiple chances for a mishap. Although there is a discussion in the Stephens et. al '417 patent concerning the use of a flat blade to incise internal tissues, there is no discussion concerning the availability or the desirability of using the flat blade of the trocar to initially incise the skin to avoid the use of a surgical sharp, and thus avoid the disadvantages attendant with this type of instrument.

Significant advances have been made in the development of surgical penetration instruments, and the methods of their insertion, but there are still risks to surmount. It would be advantageous if there was an instrument that combined a precocking shielded trocar with a surgical scalpel blade so that one instrument could be used, with increased safety, to both incise and penetrate tissue at a surgical site.

SUMMARY OF THE INVENTION

Accordingly, the present invention is a method for establishing a surgical port for use in endoscopic and arthroscopic surgery on a patient. The method comprises initially providing a trocar. The trocar is has an obturator assembly and a cannula assembly. The obturator assembly capable of being inserted into and withdrawn from the cannula assembly. The obturator assembly has an obturator, a shield, a precock lever, and a shield retaining subassembly.

The obturator has a flat cutting blade located at the distal end of the obturator. The blade has a first and a second planar surface that are generally parallel to each other and converge to a cutting edge surface. A handle is located at the proximal end of the obturator.

The shield of the obturator assembly is slideably mounted on the obturator. It is moveable from a precocked position wherein the shield is retracted and the flat blade is exposed to an extended position wherein the flat blade is covered. The shield has a shield retaining surface on it that retains the shield in the precocked precocked position to expose the flat blade and a precock surface on it as well.

The precock lever is moveable from an unactuated position wherein the shield is in the extended position and covers the flat blade to an actuated position wherein the shield is precocked to expose the flat cutting blade. The precock lever has a shield retraction surface that cooperates with the precock surface of the shield. When the precock lever is actuated the shield moves from its extended position covering the flat cutting blade to its precocked position where the flat blade is exposed.

The shield retaining assembly cooperates with the shield retaining surface of the shield. It is adapted to hold the shield in the precocked position when the precock lever is actuated.

Once the trocar is provided, the precock lever is moved from the unactuated position to the actuated position to expose the flat cutting blade of the obturator upon retraction of the shield from its extended position to its precock position. Once the flat cutting blade is exposed, the skin of the patient is incised with the flat cutting blade of the obturator. The flat blade of the trocar is inserted into the incision and a penetrating force is applied against the incised skin so that the flat blade penetrates into the internal body cavity of the patient and entry of the trocar into the body cavity of the patient is provided. The obturator assembly is then removed from the cannula assembly so a surgical access port is provided into the internal body cavity of the patient.

The method of the present invention provides a noteworthy advantage. Current surgical practices involve the use of surgical scalpels to provide the initial incision. The scalpels, or surgical sharps, are passed back and forth during the insertion of the surgical access port and the surgeon and operating room staff are exposed to the potential of an accidental nick or cut in their surgical gloves, and exposure to communicable diseases from blood or other body fluids. The "precocking" feature enables the surgeon to precock the trocar, maintain the shield in the retracted position to expose the flat cutting blade, and use the trocar as a scalpel to incise tissue. Thus, the need to handle surgical sharps to initially incise the skin is eliminated, and the trocar can be used to provide not only the surgical port, but also the sharp linear cutting surface to initially make the required skin incision.

In a particularly preferred embodiment of this invention, the surgeon can use the trocar to incise the skin using two different methods. Initially, the trocar is provided with a shield deployment mechanism which cooperates with the shield retaining assembly to release the shield from its precock position under certain conditions. When a light force is applied to the exposed blade, the shield deployment mechanism is not actuated and the incision can be completed with the blade exposed, for enhanced visibility. When a heavier force is applied to the flat blade during the incision, the retracted deployment mechanism is actuated, and the shield remains in its precock position until the penetrating force is removed, which occurs when the tissue layers of the body wall have been incised. Importantly, when this occurs, the shield snaps forward to its extended position as the result of the actuation of the shield deployment mechanism, thus providing the operator with a shielded cutting blade.

The present method of operation can be used in endoscopic, laparoscopic, and arthroscopic surgery to access to a body cavity with endoscopic surgical instrumentation. The present method is especially useful as it enhances the safety of endoscopic surgery by eliminating the need to pass surgical scalpels, or sharps, and reduces the number of instruments required for insertion of a trocar from two, scalpel and trocar, to one, a precocking shielded trocar with a flat cutting blade

DETAILED DESCRIPTION OF THE PREFERRED EMBODIMENT

Figure 1:
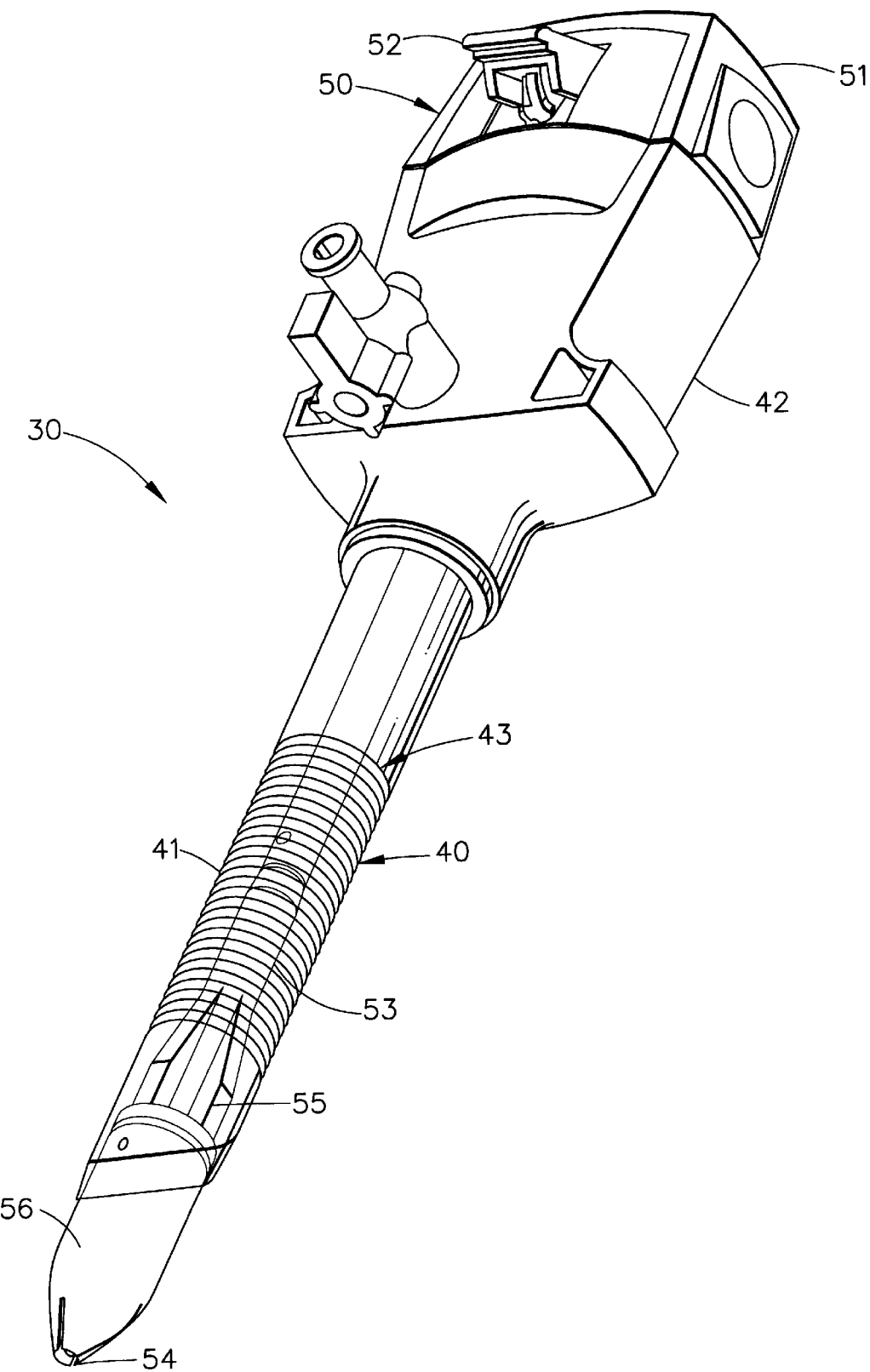
FIG. 1 is a perspective view of the assembled surgical trocar of the present invention shown in unarmed condition.
Figure 2:
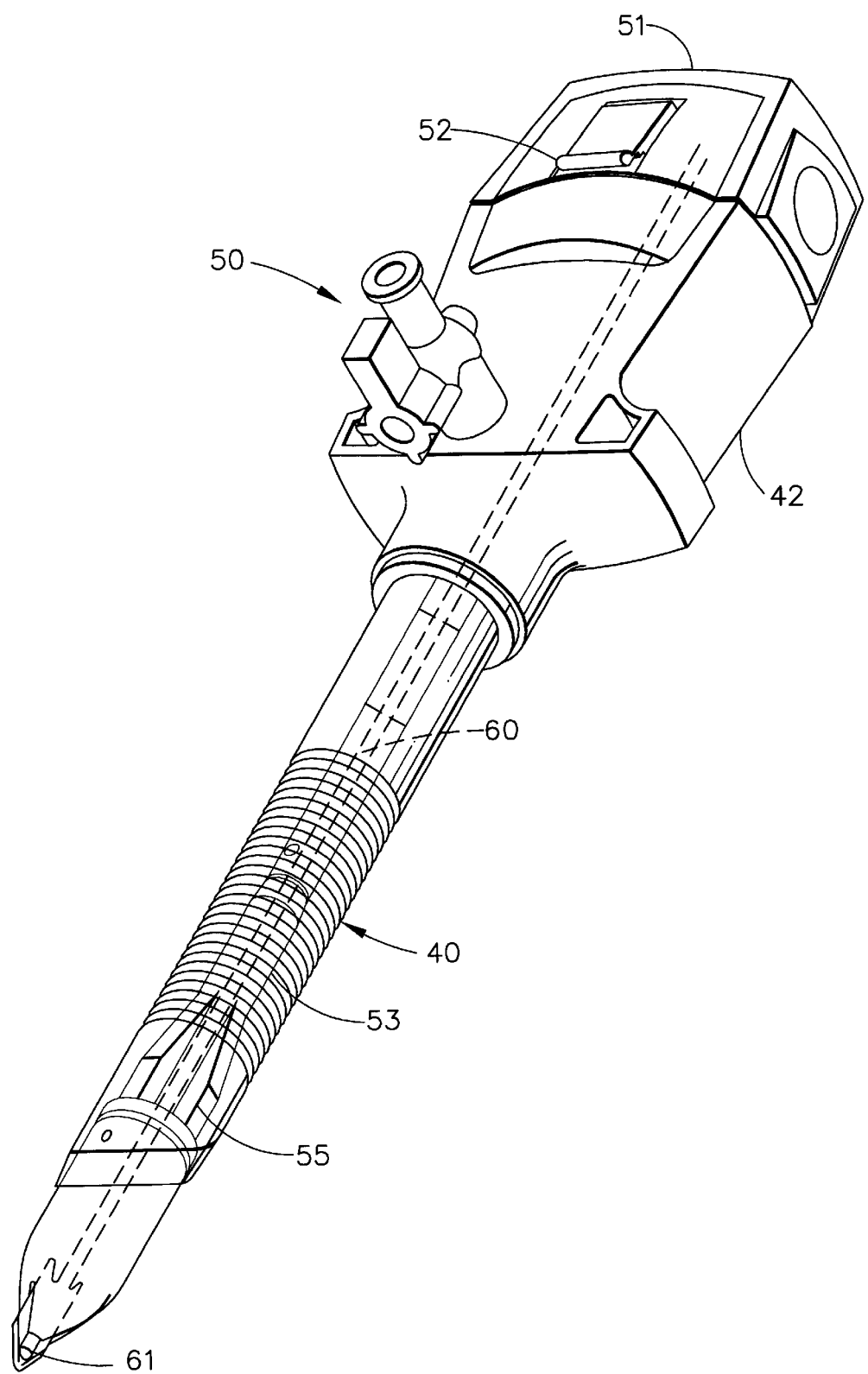
FIG. 2 is a perspective view showing the assembled cannula and obturator of the present invention in a precocked position wherein the shield is in its retracted position to expose the cutting blade.
Figure 3:
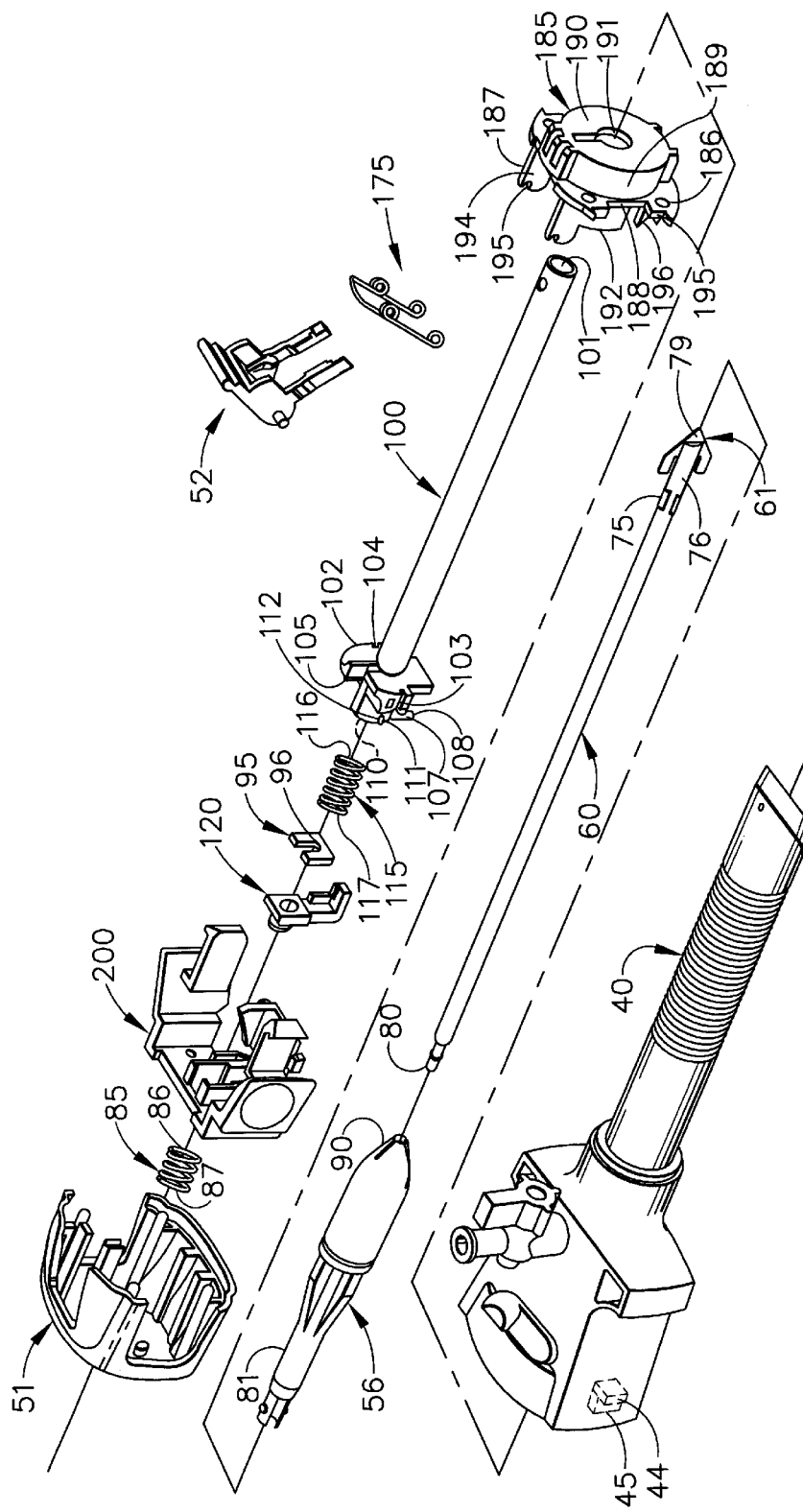
FIG. 3 is a perspective view wherein the assembled cannula is shown separate from the exploded obturator illustrating the obturator components.

As shown in FIGS. 1–3, the present invention is a surgical trocar 30 for establishment of a surgical port for endoscopic or arthroscopic surgery. The trocar 30 consists of a cannula assembly 40 and an obturator assembly 50. Cannula assembly 40 consists of tube 41, cannula housing 42, and contains a passageway 43 for receiving various members like obturators, endosurgical instruments and the like. Within this description, the portion of the instrument that is closest to the operator or surgeon will be referred to as "proximal", and that portion farther away from the operator will be referred to as "distal".

Figure 4:
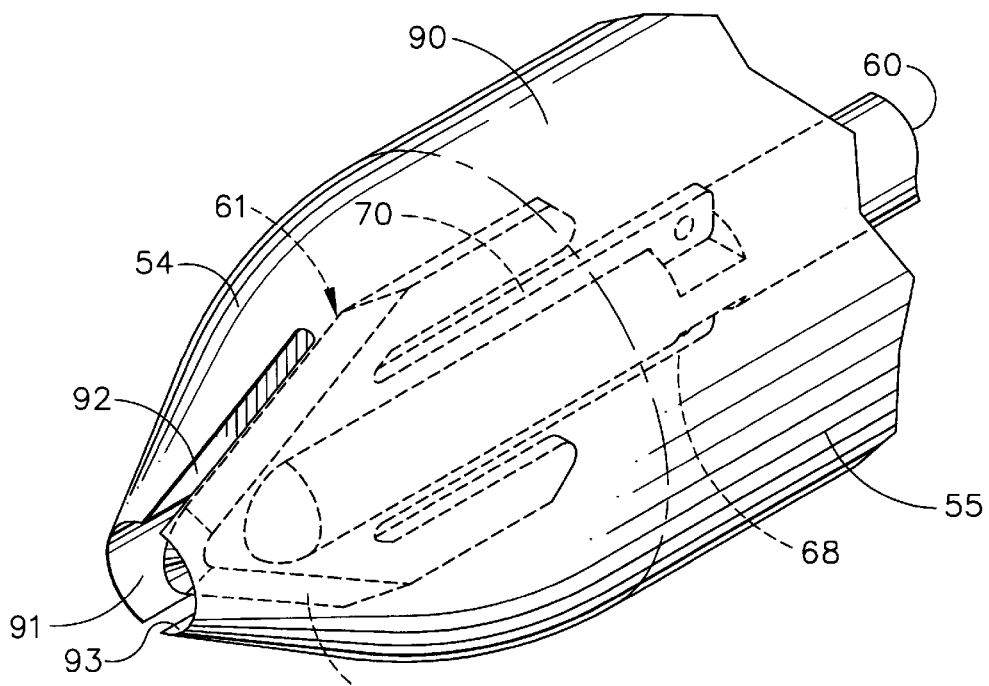
FIG. 4 is a perspective view of the distal end of the preferred obturator showing the shield in its deployed, or extended, position to cover the flat cutting blade.

Obturator assembly 50 has handle 51, precock lever 52 and obturator 53. As shown in FIG. 4, obturator 53 contains obturator shaft 60 and flat blade 61 within retractable shield 55. When the obturator 53 is fully inserted within the cannula assembly 40, handle 51 mates and locks within the cannula assembly 40 and distal end 54 of the obturator 53 protrudes from tube 41 (shown in FIGS. 1 and 2). The preferred embodiment of the cannula assembly 40 is disclosed in U.S. Pat. No. 5,387,197, which is included as a reference.

Figure 5:
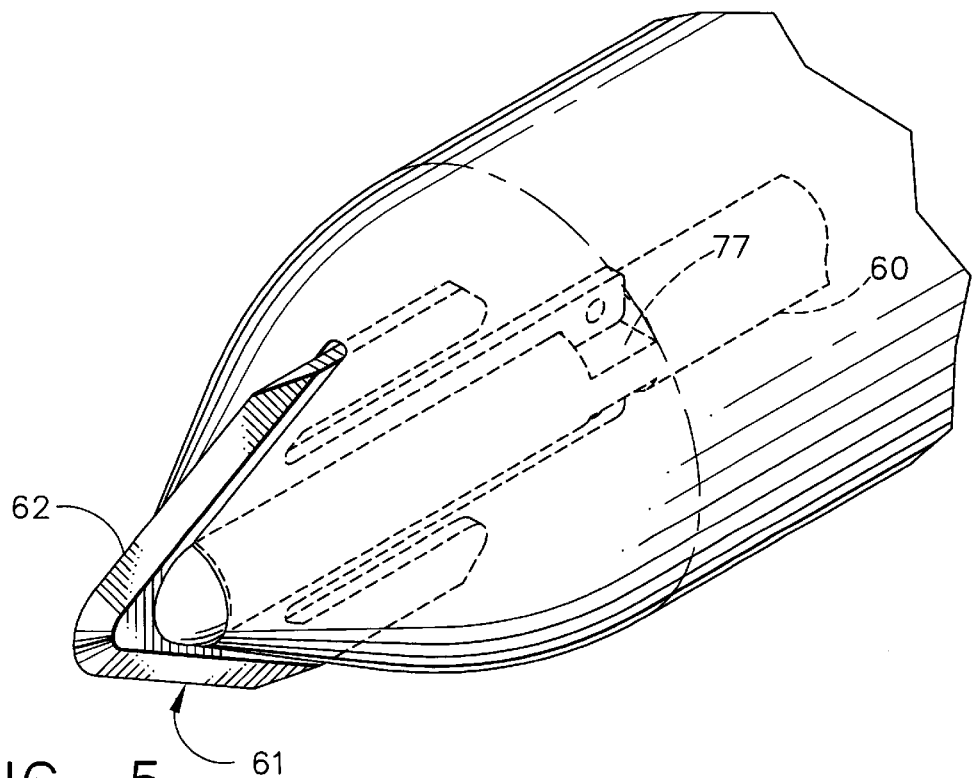
FIG. 5 is a perspective view similar to that of FIG. 4 except the shield is in its retracted position exposing the flat cutting blade of the obturator.
Figure 6:
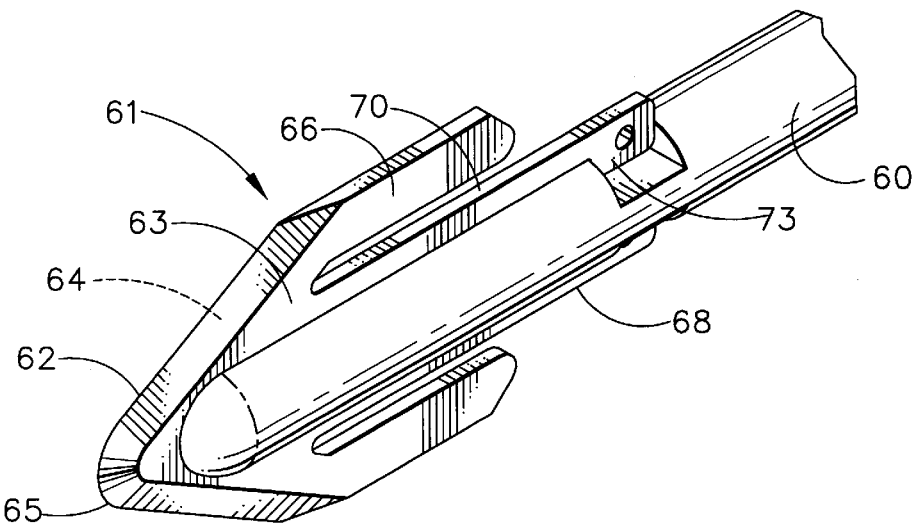
FIGS. 6–8 are perspective views of the flat blade of the present embodiment, the distal end of the obturator shaft, and the attachment of the flat cutting blade to the obturator shaft.
Figure 7:
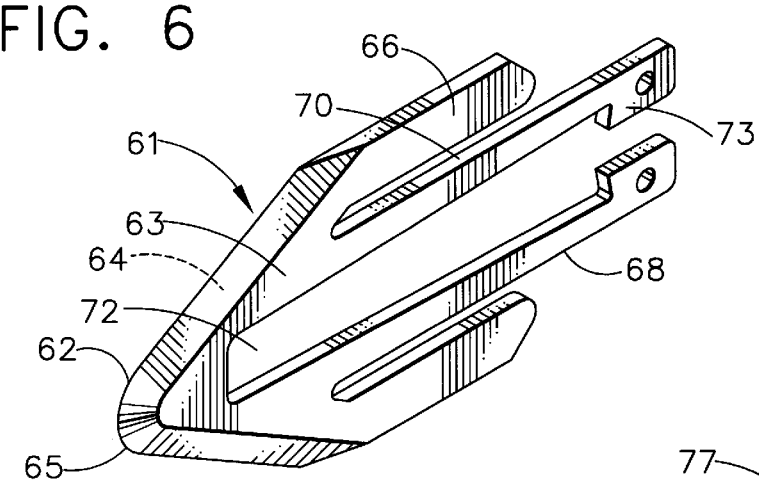

Trocar obturator assembly 50 and components are seen in FIG. 1, FIG. 2, FIG. 3, and FIGS. 3A–3D. FIG. 1 shows shield 55 in its normally deployed or extended and locked in position to cover the flat blade 61 of the obturator 53. Referring now to FIG. 2, the precock lever 52 is shown precocked or armed, shield 55 is retracted, and the flat cutting blade 61 is exposed. For this preferred embodiment, the device is precocked prior to surgery to expose the flat blade 61. The flat blade 61 has a "V" shaped cutting edge surface 62 (FIG. 5) and can be used as a surgical scalpel to incise the patient, or as a piercing or penetrating trocar tip for endoscopic or arthroscopic surgery.

The preferred cutting or piercing means is of a flat bladed design as illustrated in FIGS. 2–7. Disclosure of this preferred embodiment is described in U.S. Pat. No. 5,609,604. The flat blade has first and second planar surfaces 63 and 64, respectively, that are generally parallel to each other. The surfaces converge to form the "V" shaped cutting edge surface 62 of the piercing tip. The cutting edge surface is triangular in shape, and has a rounded apex 65. Extending proximally from the triangular cutting surfaces, are first and second elongated arms 66. Additionally, first and second legs 68 extend in a direction away from the cutting edge surface of the cutting tip. The legs are spaced apart from each other, and are generally parallel to each other. The legs are located interior of the elongated base portions. Longitudinal slots 70 separate the elongated arms from the legs. The distance between the legs defines an interior slot 72 within the flat blade. At the end of the first and second legs, there are mutually opposed, inwardly extending barbs 73.

Figure 8:
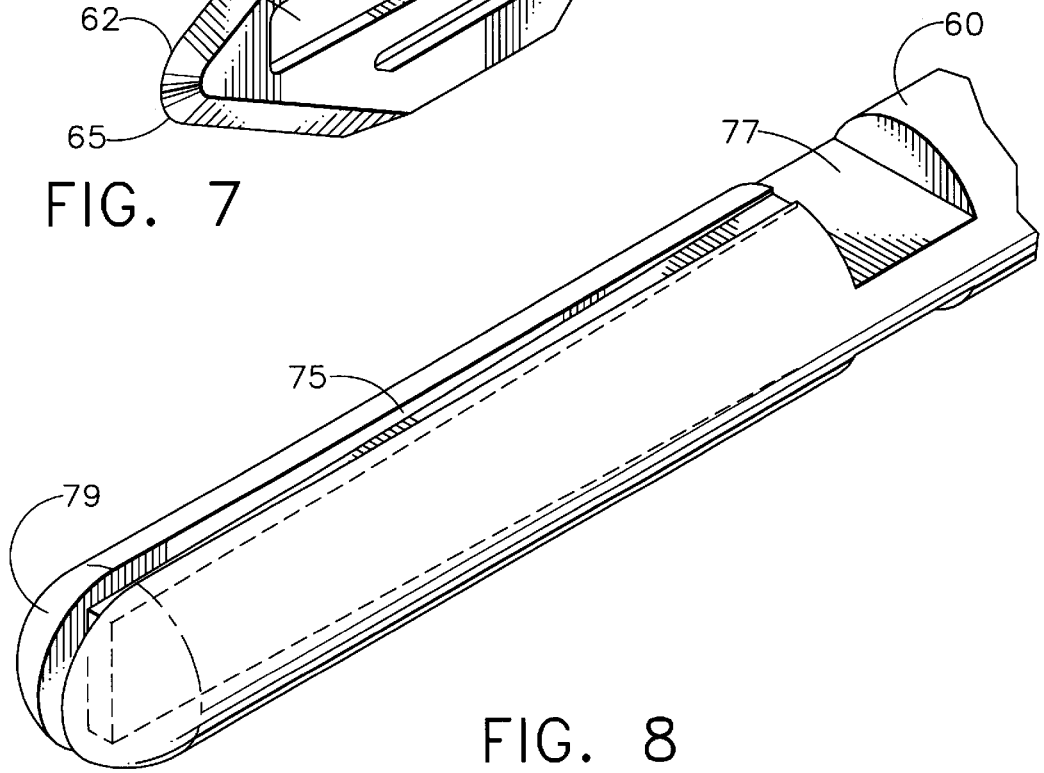

Referring to FIG. 8, the rounded distal end 79 of obturator shaft 60 has stabilizing slots 75 and retention notches 77 for attaching the flat blade to the obturator shaft. The stabilization and retention features allow the obturator to be easily configured with a variety of flat blades. The flat blade 61 is rigidly mounted to obturator shaft by sliding the legs 68 into the slots 75 until the barbs 73 are captivated in the notches 77.

The obturator shaft 60 is slidably mounted within the shield 55. Proximal end 80 of obturator shaft 60 is displaceable into a cavity 147 in the interior proximal wall of the obturator handle 51. In the precocked condition, wherein the blade is exposed, the flat blade 61 has range of proximal and distal motion, or stroke, with respect to the handle 51. Proximal motion of the exposed flat blade 61 and obturator shaft 60 unlocks the shield retention mechanism. A lesser amount of distal motion, or stroke, of the blade, with the shield retention mechanism unlocked, allows the shield 55 to deploy distally to encase the exposed flat blade 61. Some proximal and distal stroke amounts are required to activate the shield deployment mechanism, but it is preferred that the amount is variable depending on device configuration or device size and is not deemed to be critical to the intent of the design. For this preferred embodiment, the proximal stroke required to unlock the shield retention mechanism is approximately 0.040 inches plus and minus 0.030 inches. To deploy the shield 55, the distal stroke amount is between 0.005 to 0.040 inches.

Referring to FIGS. 1 and 3, shield 55 is an elongated tubular member that is concentric to and slidably mounted on obturator shaft 60. Safety shield is comprised of a tip 56 and a tube member 100 and contains an axial passageway 101 for the obturator shaft 60. The tip 56 is fixably mounted to the tube member 100. The distal end 90 of the tip 56 is preferably bullet shaped and encases the flat blade 61. The distal tip axial passageway 101 consists of a generally circular central opening 91 and a first and second vertical slot 92 and 93, respectively, for the encasement of the flat blade (see FIG. 4). The distal end 90 of the obturator, the central opening 91 and the slots 92, and 93, are shaped to envelop the particular size or configuration of the flat blade 61. While the bullet shape is the preferred embodiment, the shape of the distal tip for shielding the knife can be a number of shapes and still meet the design intent.

Figures 9, 10:
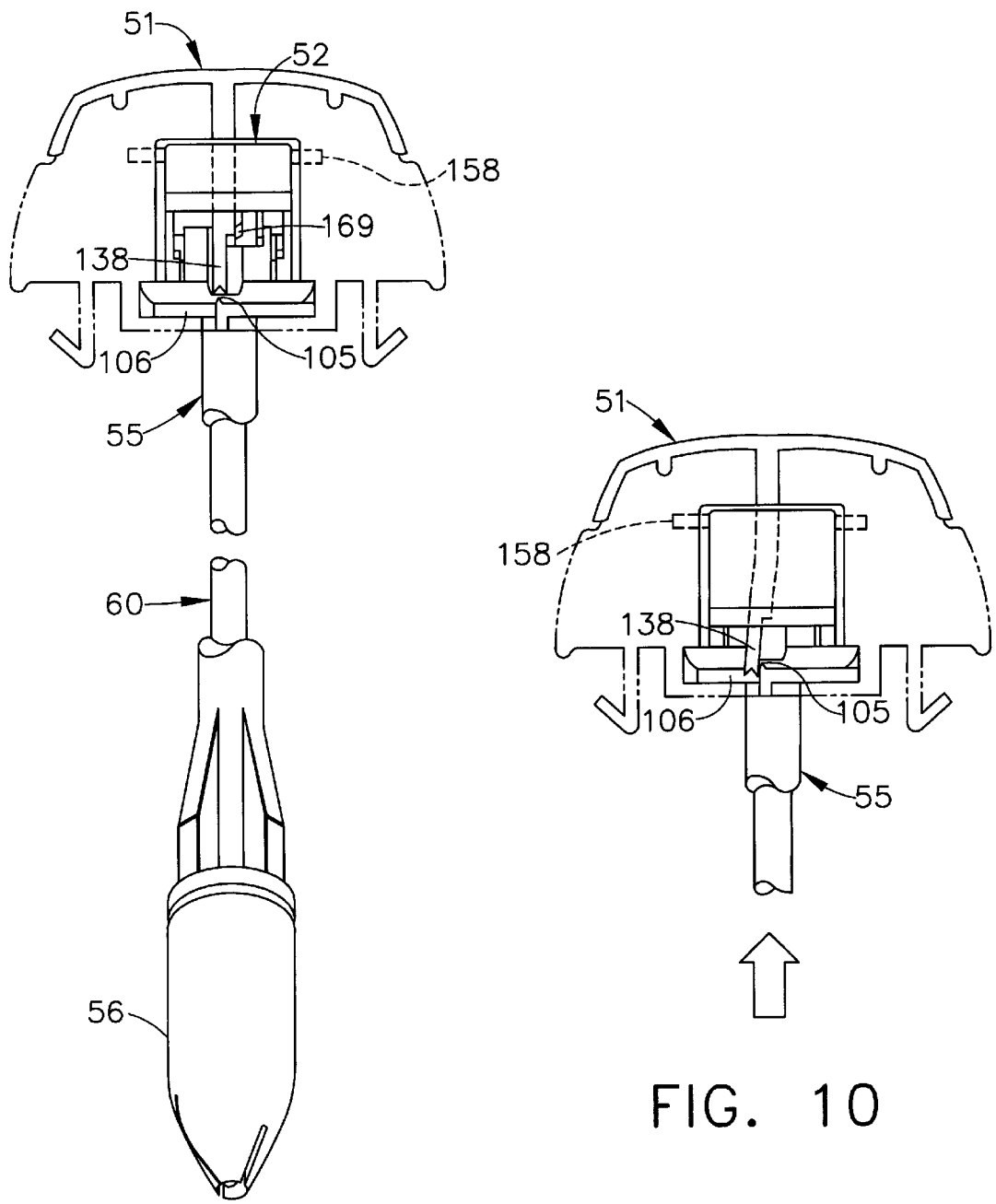
FIG. 9 is a partial cross sectional view of the trocar of the present invention in an uncocked condition wherein the shield locking arm is in a locked position and the precock lever is fully extended.
FIG. 10 is a partial cross sectional view of the trocar of the present invention in a partially cocked condition wherein the precock lever is partially depressed inwardly, and the shield locking arm is deflected enabling proximal motion of the shield to expose the flat blade (not shown).
Figure 11:
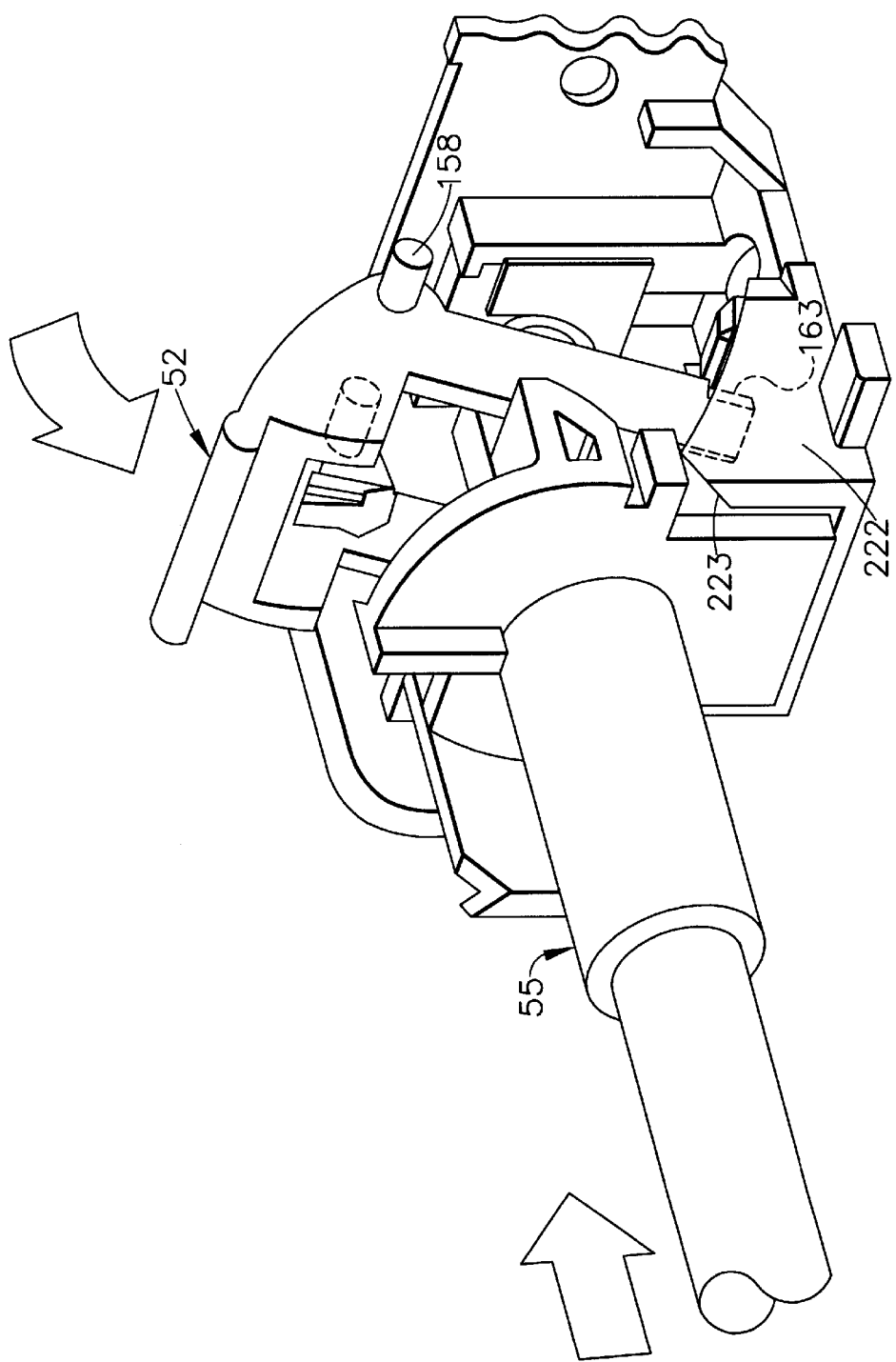
FIG. 11 is a partial perspective cross sectional view of a partially precocked trocar of the present invention wherein the parallel arms of the precock lever are deflected inwardly, to engage and retract the shield, by the triangular plates of the latch plate; the handle and latch are partially cut away.
Figure 12:
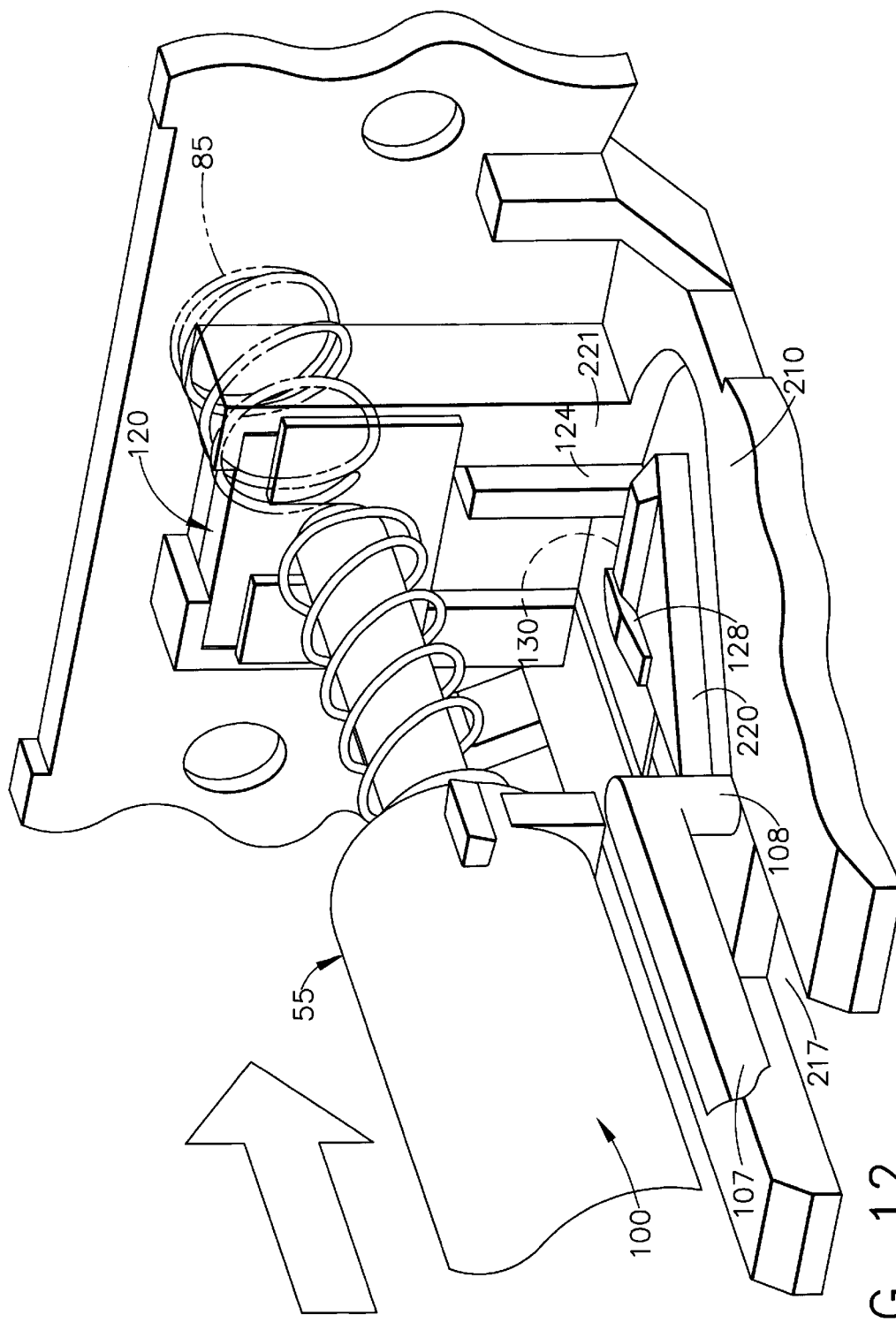
FIG. 12 is a partial perspective cross sectional view of a partially precocked obturator of the present invention wherein the shield is partially retracted and the locking pawl has just entered the angled channel located in the latch plate of the latch; the handle and latch are partially cut away and the precock lever is removed for clarity.
Figure 13:
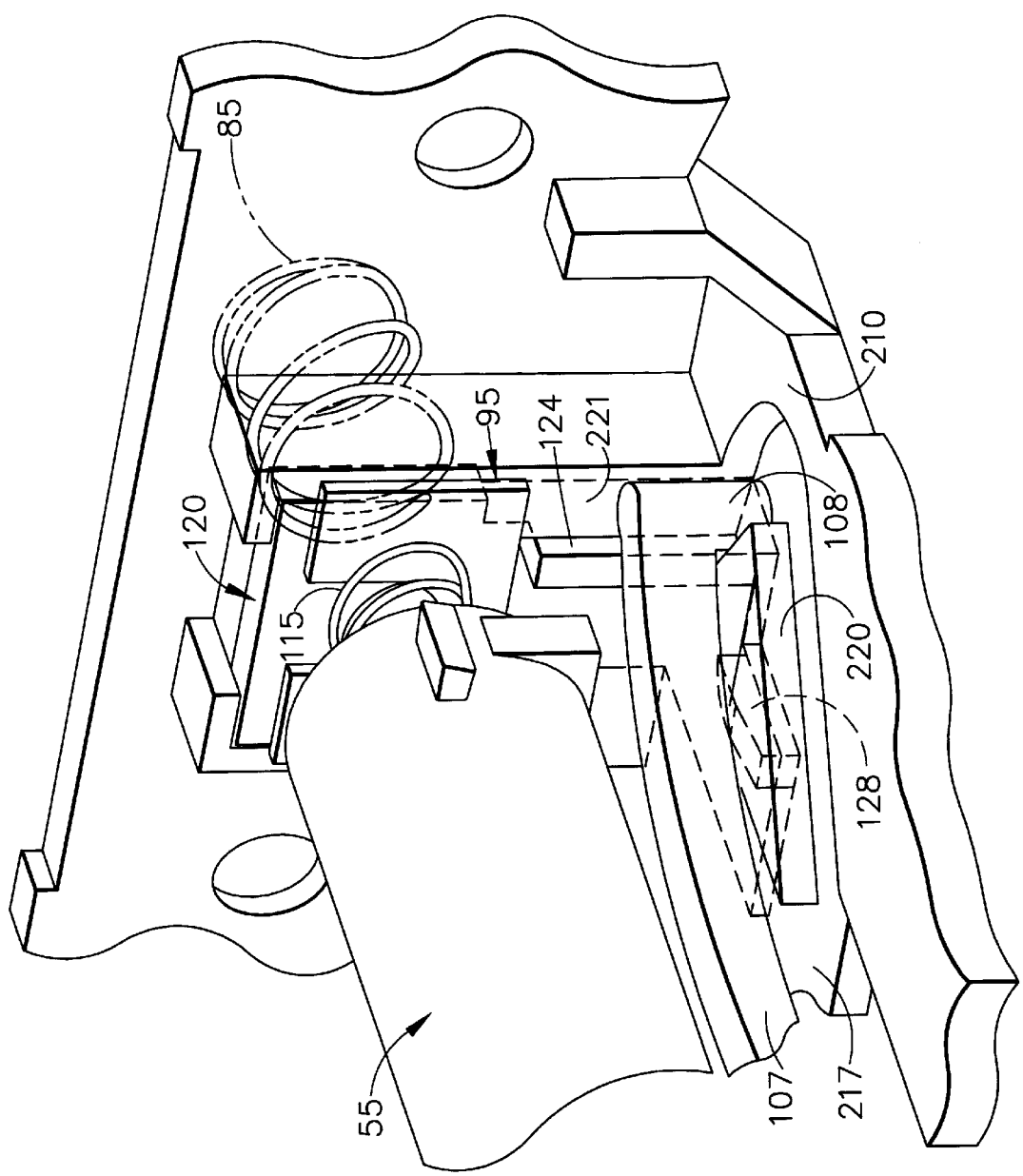
FIG. 13 is a partial perspective cross sectional view of a precocked, or armed, obturator of the present invention wherein the locking pawl is in the cross channel, abutting the first contact surface of the knife collar, and the shield is fully retracted; the handle and latch are partially cut away and the precock lever is removed for clarity.

The proximal end of tube member 100 has a radially outward extending end flange 102. The end flange 102 has fin members 103 with slots 104 to provide stability during sliding. End flange 102 also includes shield locking tooth surfaces 105, cutout 106 (FIGS. 9 and 10), and shield retention arm 107. Pawl 108 extends outwardly from the free proximal end of the generally rectangular elongate shield retention arm 107. Extending proximally from the center of the end flange 102 is a generally tubular spring mount 109 with a central bore 110. The bore 110 is concentric to and larger than the axial passageway 101 and extends from the proximal end of the spring mount 109 to the proximal surface of the end flange 102. The distal end of bore 110 forms step face 113 with axial passageway 101. Precock ramp ribs 111 are mutually opposed and extend from the surface of the tubular spring mount 102. Precock ramp surfaces 112 are located on the distal face of the ramp ribs 111.

A compression type shield spring 115 mounts concentrically on the proximal end 80 of the obturator shaft 60. Distal end 116 of the spring 115 mounts concentrically within bore 110 and abuts step face 113. Proximal end 117 of the spring 115 abuts spring stop 95. Spring stop 95 is a "U" shaped plate with a circular slot 96 that extends radially from the center. The spring stop is concentrically mounted on obturator shaft 60 between knife collar 120 and shield spring 115. Shield spring 115 is normally compressed between the central bore step face 113 and the spring stop 95 to provide a distal biasing force against the slidably mounted shield 55. The shield 55 is moveable between a fully extended position, wherein the flat blade of the obturator is enveloped, and a fully retracted position wherein the flat blade is exposed.

Figure 3A:
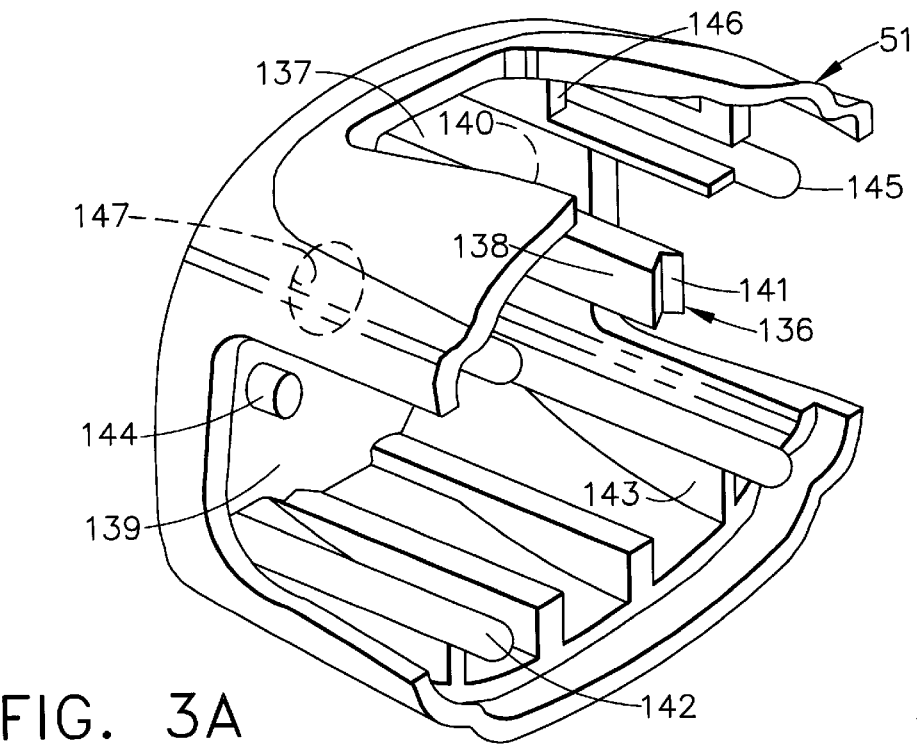
FIGS. 3A–3D are enlarged perspective views illustrating obturator components as shown in the exploded view of the obturator (FIG. 3).
Figure 3B:
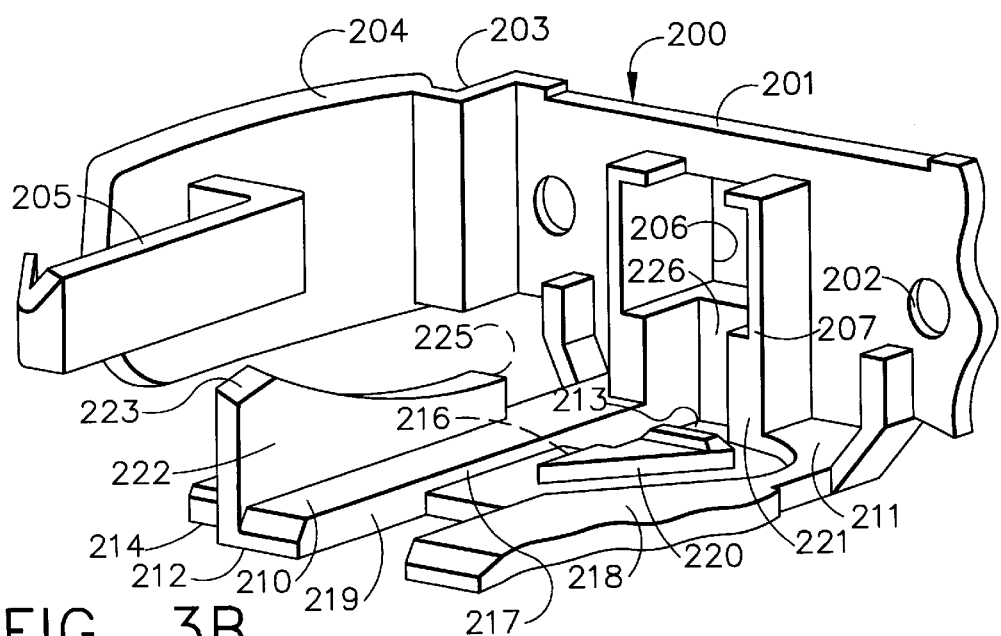
Figure 3C:
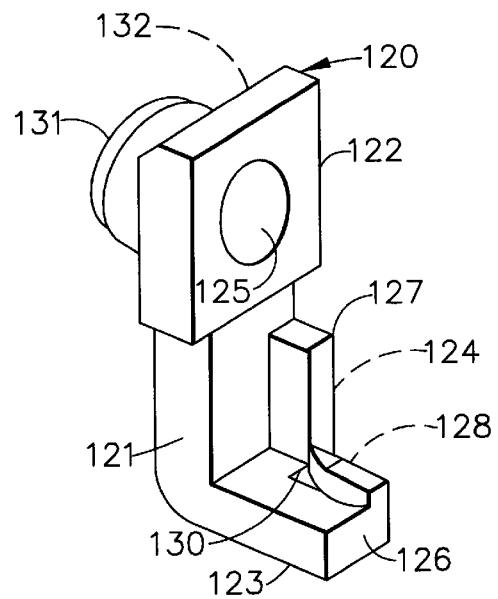

Referring specifically to FIG. 3C, knife collar 120 is fixedly mounted to the proximal end 81 of the obturator shaft 60. Knife collar 120 is made up of a block 122 with a circular hole 125 extending through. Arm 121 extends axially from the concentrically mounted block 122 and includes hook 123 extending distally from the distal face of the free end of arm 121. Knife collar surface 126 is located on the distal end of the hook 123. Pawl contact surface 128 is located on the inward side of hook 123. Rib 127 extends from the distal surface of the generally free end of the arm 121 and is opposably located from the hook 123. The rib 127 forms pawl contact surface 124 with the arm 121. Pawl slot 130 is longitudinally located between the pawl contact surface 128 and the pawl contact surface 124. An annular member 131 extends proximally from the proximal surface of the block 122 with circular hole 125 extending therethrough.

The distal end 86 of knife spring 85 abuts the proximal side of the block 122 of the knife collar 120, and is concentrically mounted on annular member 131. The proximal end 87 of knife spring 85 mounts within cavity 147 in the interior proximal wall of the obturator handle 51. Knife spring 85 provides a distal biasing force against the knife shaft assembly consisting of collar 120, the obturator shaft 60 and the flat blade 61. As previously mentioned, the components are axially moveable in a precocked condition, between a fully extended distal position wherein the blade is exposed, and a proximal position wherein the shield retention mechanism is unlocked. The spring 85 limits the axial motion of the knife blade 61 by applying a distal biasing force to offset the opposing proximal force caused by tissue contact at the flat blade 61, and biases the knife shaft assembly from its most proximal position, in the handle 51, distally to actuate the shield deployment. It is preferred that the biasing force exerted by the spring 85 is changeable to meet the wide range of tissue contact forces that this present invention can experience, and still function in a safe and efficacious manner. As a consequence, the spring biasing force is not deemed to be critical as to the intent of the design, but should be allowed to vary to meet a wide range of tissue contact forces. The tissue contact force applied to the flat blade 61 can range from 0.1 to over 10 pounds. For this preferred embodiment, the spring is sized to deflect 0.040 inches (full stroke) for an approximate 1.00 pound tissue contact force applied to the flat blade.

Referring to FIG. 3A, trocar obturator handle 51 is a hollow member containing interior cavity 135. The distal end of the handle is open and receives end cap 185. Open latch slots 136 are generally rectangular in shape and are mutually opposed and centrally located on the sides of the handle 51. Open precock lever slot 137 is rectangular in shape and centrally located on the top of the handle 51. Elongated rectangularly shaped shield locking arm 138, extends distally from the proximal interior wall 139 and is generally centrally located in the precock lever side slot 137. Angled unlocking ramp surface 140 extends axially and distally from the proximal interior wall 139 along most of the beam. Locking groove 141 is generally "V" shaped and extends along the distal end of the free end of the locking arm 138. Locking groove 141 normally engages locking tooth 105 located on the flange 102 of the tube member 100 to lock the shield in the extended position. Extending axially and distally from the interior proximal wall 139 are cap mounting posts 142, cap mounting post ribs 143, and the latch mounting posts 144. A pair of precock lever mounting slots 145 are opposedly located on the interior of the handle 51 on either side of the precock lever slot 137. The slots abut the interior wall, extend laterally and distally, and contain precock trigger bearing surfaces 146. The flat bearing surfaces 146 are located proximally in the slots 145 and form one side of the generally circular bearing for pivot pins 156 on precock lever 155.

Figure 3D:
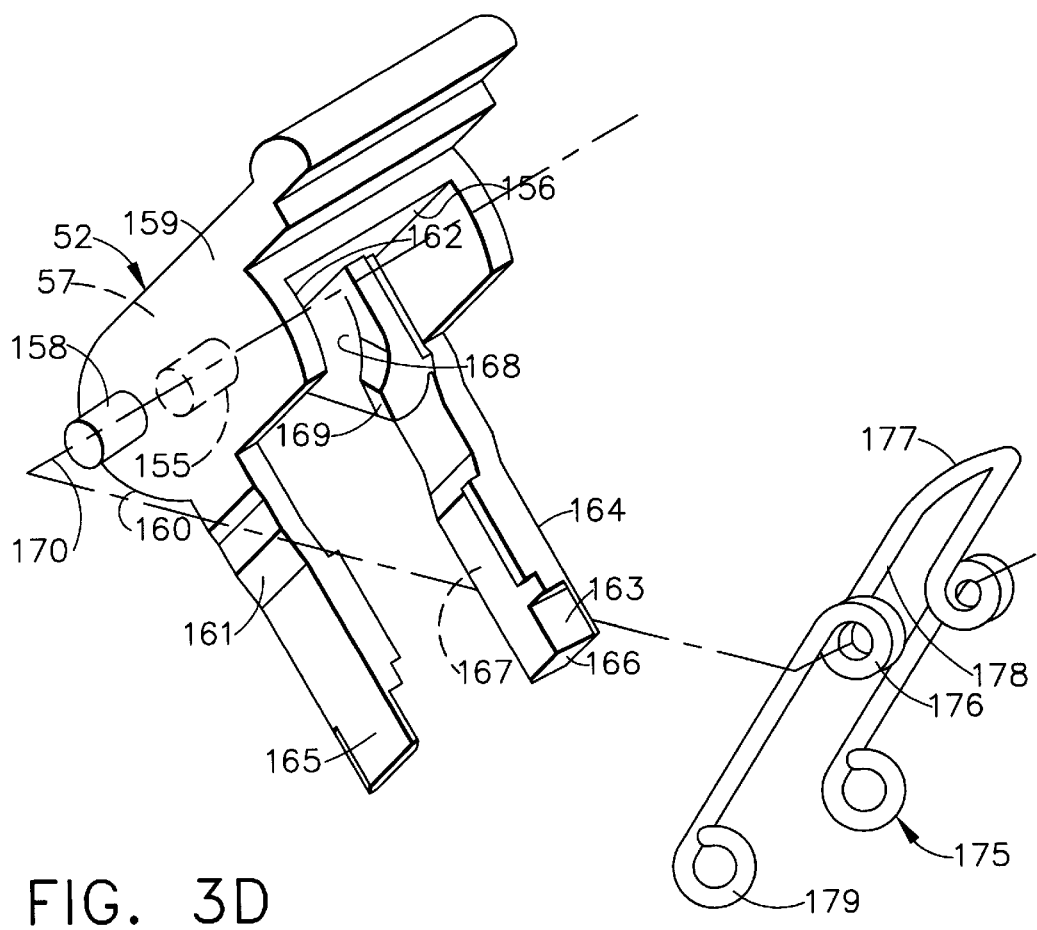

Referring specifically to FIG. 3D, precock lever 52 is a generally rectangular plate 156 that is pivotally mounted in the obturator handle 51. Exterior lever face 157 provides an operator contact surface to unlock the sliding shield, retract the shield, and activate the shield retention mechanism. A pair of pivot pins 158 extend outwardly from the plate sides 159 near the proximal end 160. The precock lever 52 mounts in the precock lever slot 137 and the pivot pins 158 pivotally mount into the lever pin slots 145. A pair of flexible elongated generally parallel arms 161 extend outwardly from the interior face 162 of the lever, at the outer sides of the proximal end 160 of the plate 156, and at a generally obtuse angle with the plate 156. A pair of ramped surfaces 163 are inwardly ramped on the distal side 164 of the free ends 166 of the parallel arms 161. An additional pair of ramped surfaces 165 are outwardly ramped on the proximal side of the free ends 166 of the parallel arms 161. An opposed pair of shield retraction rib surfaces 167 extend inwardly from the inward faces of the parallel arms 161. These rib surfaces 167 contact the precock ramp surfaces 112 located on tube member 100 to retract the shield 55 when the precock lever 52 is precocked or actuated. A generally rectangular unlocking beam 168 flexibly extends inwardly from the general center of the interior lever face 162. Ramped unlocking surface 169 is pivotally located around the lever pivotal axis 170 on the side of the unlocking beam 168. A pair of opposed spring pins 155 extend inwardly near the fixed ends of the parallel arms 161.

Lever spring 175 provides a biasing force to keep the precock lever 52 pivoted outward from the handle 51. This ensures the return of the lever to the uncocked position. The spring 175 consists of a pair of torsion springs 176 joined together at the ends by connector 177. The coils of the torsion springs 176 are placed circumferentially over the lever spring pins 155, with the connector 177 and the connected ends 178 of the torsion springs abutting the interior lever face 162. While the preferred embodiment is a pair of torsion springs, any other spring such as a cantilever, compression or other could provide the biasing force and still meet the design intent. The free ends 179 of the spring 175 are formed in an arcuate shape.

Referring now to FIG. 3, end cap 185 is a generally "H" shaped flat plate that mates with the open distal end of the obturator handle 51 to enclose the distal end of the handle 51. Circular openings 186 are circumferentially located to receive the distal ends of the end cap mounting posts 142. Rectangular lever opening 187 is located on the edge of the exterior of the end cap 185 and is aligned with the precock lever slot 137 on the handle 51. Rectangular latch slots 188 are laterally opposed and extend outwardly to provide clearance for the latch. Cylindrical member 189 extends distally from the end cap 188 and is capped on the distal end by end plate 190. Central cylindrical circular opening 191 extends through the distal end plate 190. End members 192 extend from the end cap and have rib guides 193 for guiding and stabilizing the shield 55. Guides 193 are slidably engaged with slots 104 located in the end flange 102 of tube member 100. Generally parallel end members 194 extend proximally from the end cap with circular lever bearing slots 195 extending proximally. When handle 51 and end cap 185 are assembled, the precock lever pivot pins 158 are pivotally captured between the lever bearing slots 195 and the precock trigger bearing surfaces 146. The free end 212 of the latch 200 is constrained in slots 195 between pairs of guide teeth 196 that extend proximally from the end cap 185.

Referring to FIG. 3B, latch 200 consists of a generally plate like connector beam 201 that is rigidly mounted to the proximal internal wall 139 of the obturator handle 51. Circular openings 202 receive the ends of the latch mounting posts 144. A pair of latches 203 flexibly extend distally from the connector beam 201. The latches are of living hinge type or cantilever type construction. Finger pads 204 and tab members 205 are axially located on the latches. Finger pads 204 extend through and are centrally located within the latch slots 136 in the obturator handle 51. Rectangular opening 206 is centrally located in the connector beam 201 and extends therethrough. Parallel spring stop ribs 207 are located laterally on either side of the rectangular opening 206 and extend distally from the distal surface of connector beam 201. The obturator 53 is insertable within the handle 51 and the proximal face of the spring stop 95 abuts the distal faces of the spring stop ribs 207. The spring stop 95 is proximally biased by compression shield spring 115. The contact of the spring stop 95 with the spring stop ribs 207 isolates the proximal end of the obturator shaft 60, knife collar 120, and the compression knife spring 85 from the biasing force from shield spring 115. As previously described, the knife spring 85 applies a distal biasing force to the knife collar 120 and the proximal end 80, of obturator shaft 60, is displaceable into cavity 147 in the interior proximal wall of the obturator handle 51.

The latch plate 210 extends centrally and distally from the bottom of the latch connector beam 201. The latch plate 210 is a generally rectangular elongate beam with a fixed proximal 211 and a free distal end 212. The free distal end 212 is constrained by inserting tabs 214 within the slots 195 located in end cap 185. An "L" shaped opening 213 is generally centrally located in the fixed end 211 of the latch plate 210 and extends therethrough. The "L" shaped hook 123, located on the free end of the knife collar 120, mates within "L" shaped opening 213, and is free to travel proximally and distally within the opening 213. The knife collar surface 126, located on the distal end of the hook 123, is normally biased against the distal end 216 of the opening 213 by the knife spring 85. Proximal motion of the knife collar 120 is limited by the contact of the proximal surface 132 of the knife collar arm 121 with the proximal surface 226 of the "L" shaped opening 213.

A recessed channel 217 located on the inward surface 218 of the latch plate 210 extends distally from the long leg of the "L shaped slot 213 and connects with slot 219 that extends through the latch plate 210. Recessed angled channel 220 is angularly extended outward from the channel 217 and is connected to a cross channel 221 that intersects the short leg of the "L" shaped slot 123. The three channels, channel 217, angled channel 220, and cross channel 221, form a generally triangular path for the pawl 108. A pair of parallel generally triangular plates 222 extend inwardly from the inner surface of the latch plate 210. A pair of inwardly ramped surfaces 223 are located at the apexes of the triangles to inwardly deflect the parallel arms 161 of the lever. A pair of outwardly ramped surfaces 225 are located proximally on the triangular plates to outwardly deflect the parallel arms 161 of the lever.

The assembly of the trocar obturator 50, as shown in FIG. 3, is performed in the following manner. Components are assembled in a series of sub assemblies that are brought together with individual components to produce the preferred embodiment. First, the tube member 100 is fed through the circular opening 191 in the end cap 185. Next, the proximal end of bullet tip 56, is fixedly assembled onto the distal end of the tube member 100 to form shield 55. The means of assembly is not critical to the intent of the design and could consist of welding, snapping, bonding, threading, and the like. Flat blade 61 is attached to the distal end of obturator shaft 60 by sliding the legs 68 of the blade rearwardly in slots 75 until the barbs 73 lock into place in notches 77. This method provides a secure attachment that is resistant to torquing and high loads. Other methods of attachment are possible such as welding, bonding, and the like. The proximal end of the obturator shaft 60 is inserted into the opening 91 in the distal end of the shield 55. Shield spring 115 is concentrically mounted onto the distal end of the obturator shaft 60. Next, the slot 96 of spring stop 95 is placed around the proximal end of the obturator shaft 60, and abutting the proximal end of spring 115. The knife collar 120 is attached to the proximal end of the obturator shaft 60, compressing the shield spring 115. The spring is captured between the spring stop 95 and the knife collar 120. The knife collar 120 is attached with conventional attachment methods such as press fit, ultrasonic welding, adhesives, brazing and the like. The latch 200 is mounted onto the handle mounting posts 144 located in the handle 51, and secured in place by ultrasonic welding, adhesives, snap fit, and the like. Next, the knife spring 85, is placed into cavity 147 within the handle 51. Then, the obturator sub assembly is placed within the handle sub assembly with the knife collar 120 placed in concentric engagement with the knife spring 85, and with the knife collar hook 123 placed in slidable engagement with the opening 213 of the latch plate 210. Next, the lever spring 175 is mounted on the precock lever 52 by placing the coils of the torsion spring 176 circumferentially over the lever spring pins 155. Then, the precock lever 52 pivot pins 158 are dropped into the lever pin slots 145 located in the handle 51, and the parallel arms 161 of the precock lever 52 are placed straddling the tube member 100, between the fin members 103 and the ramp surfaces 112. The arcuate ends 179 of the lever spring 175 are placed in angular contact with the distal face of the latch 200 as the precock lever 52 is placed. Finally, the end cap 185 is mounted onto the distal end of the handle 51 by placing the end cap 185 onto the mounting posts 142 in such an orientation that the pivot pins of the precock trigger 52 are captivated within the end cap slots 195. The end cap is then secured into place using conventional methods such as those described above.

The trocar 30 is assembled for use by inserting the bullet shaped distal tip 56 of an unarmed obturator 53 within the proximal end of passageway 43 located in the cannula assembly 40. As described previously, the cannula assembly 40 is disclosed in U.S. Pat. No. 5,387,197, which is included as a reference, and can contain sealing gasket rings, flapper valves, vacuum ports and the like. For this embodiment, the cannula 40 contains latch openings 45 and cavities 44 such that the tab members 205, of the obturator latch 200, can enter the latch openings 45 and engage the cavities 44. This locks the trocar obturator assembly 53 with the cannula assembly 40 to make trocar 30.

The trocar 30 operates in the following manner (see FIGS. 9–16). The trocar 30 is precocked by depressing the distal end of the precock lever 52 inwardly. This motion unlocks the locking arm 138 that restricts the shield 55 from axial motion. As the precock lever 52 pivots about the pivot pins 158, the ramped unlocking surface 169 located on the precock lever 52 moves arcuately to contact the ramped surface 140, located on the locking arm 138. This contact deflects the locking arm 138 away from the locking tooth 105 and into the cutout 106 located on the tube member 100, and the shield 55 is free to move proximally. Simultaneous with this motion, the outwardly ramped surfaces 163, located on the parallel arms 161 of the precock lever 52, contact the inwardly ramped surfaces 223 located on the latch, to deflect the parallel arms 161 inwardly toward the spring mount 109. The inward and arcuate motion of the parallel arms 161 brings the shield retraction rib surfaces 167, located on the inward sides of the parallel arms 161 of the precock lever 52, into contact with the ramp surfaces 112 located on the tube member 100. As the precock lever moves throughout its arc, this contact moves the shield 55 proximally, compressing the shield spring 115, to expose the blade.

Figure 14:
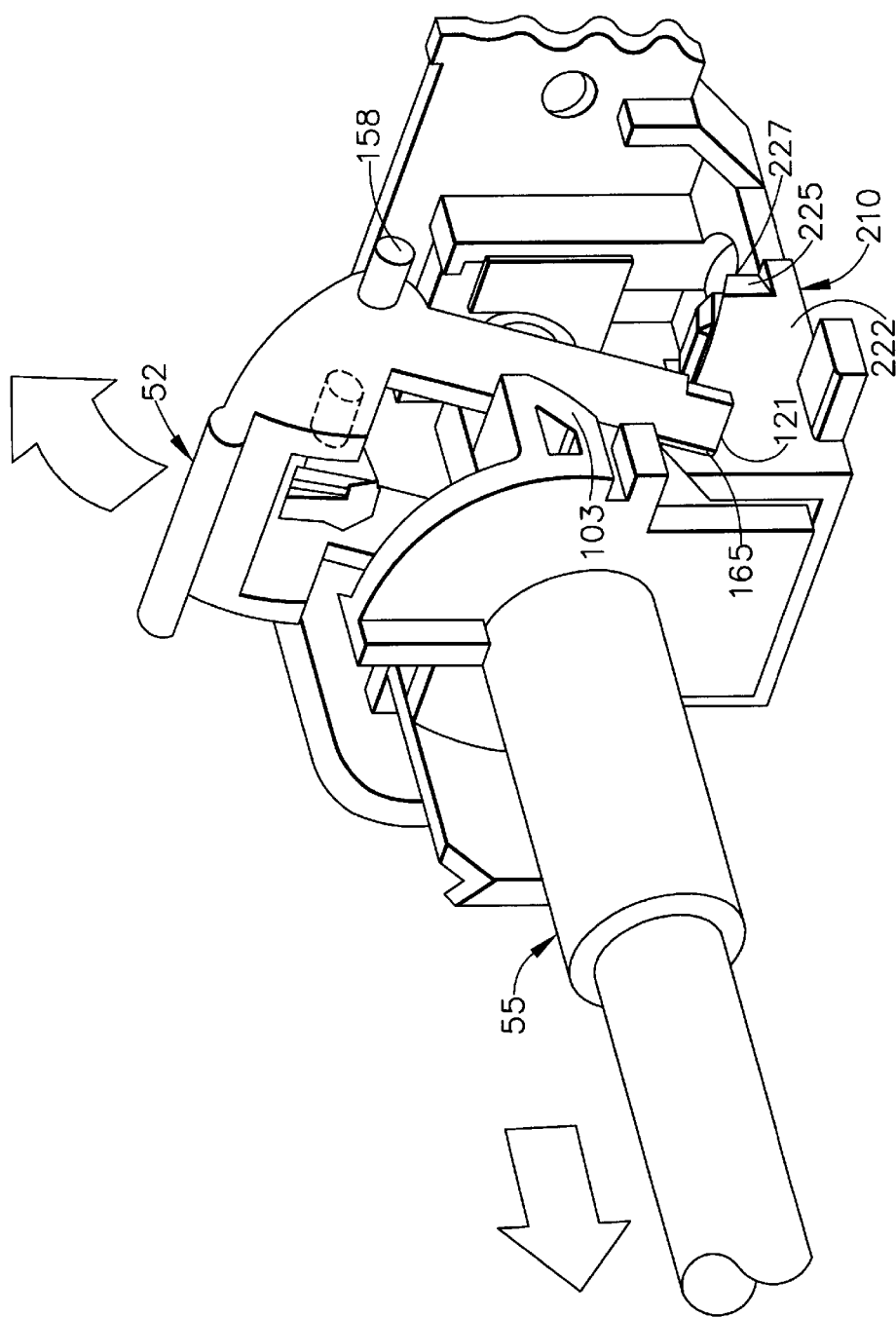
FIG. 14 is a partial perspective cross sectional view of a fully precocked, or armed, trocar of the present invention wherein precock lever is in the intermediate position and the parallel arms of the precock lever are deflected outwardly, disengaged from the shield, by the triangular plates of the latch plate; the handle and latch are partially cut away.

As the shield 55 moves proximally the pawl 108, located on tube member 100 travels proximally in longitudinal channel 217 until it enters the angled channel 220, located in the latch plate 210. As the pawl 108 follows the angled channel 220, the arm 107 is flexibly deflected. When the pawl 108 enters the cross channel 221, the deflected arm 107 moves the pawl 108 inwardly to contact surface 124 located on the knife collar 120. Full deflection of the precock lever 52 enables the free ends 121 of the parallel arms 161, located on the precock lever 52, to spring past the proximal ends 227 of the triangular plates 222, and deflect outwardly to the normal parallel condition. The outward motion of the parallel arms 161 moves the shield retraction rib surfaces 167, away from contact with the ramp surfaces 112, and disengages the shield from the precock lever. Upon release from the arms 161, the shield moves distally under the shield spring 115 bias, until stopped by contact of the distal side of the pawl 108 with the distal side of the cross channel 221. The arm 107 remains deflected with the pawl 108 abutting surface 124 on the knife collar 120. At this point the trocar 30 is precocked, the shield 55 is retracted, and the flat blade 61 is exposed. Release of the precock lever 52 by the operator, enables the lever spring 175 to bias the distal end of the precock lever 52 to an intermediate position as shown in FIGS. 2 and 14. As the precock lever 52 is biased to the intermediate position, the ramped surfaces 163 on the parallel arms 161 contact the outwardly ramped surfaces 225 on the latch plate 210 and outwardly bias them as the arms swing through an arcuate path until they abut the proximal side of fin member 103 and stop the precock lever 52 at the intermediate lever position. This position indicates the trocar 30, is precocked and ready for use. Further deflection of the precock 52 lever produces no effect on the unloaded, pre-cocked trocar 30.

Figure 15:
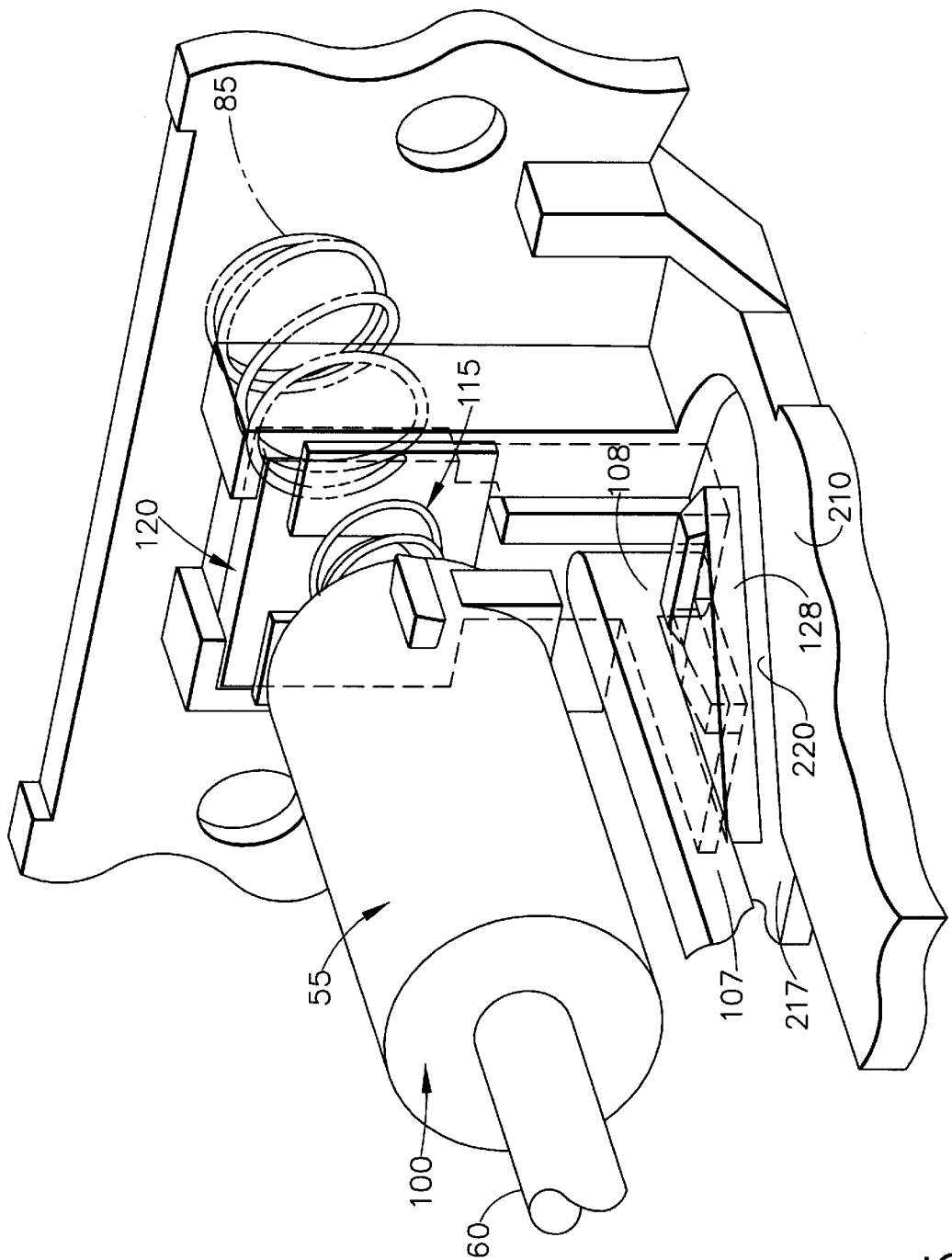
FIG. 15 is a partial perspective cross sectional view of a precocked (armed) obturator of the present invention wherein the knife collar and obturator shaft are moved proximally, enabling the locking pawl to abut the second contact surface of the knife collar, unlocking the shield for deployment; the handle and latch are partially cut away and the precock lever is removed for clarity.
Figure 16:
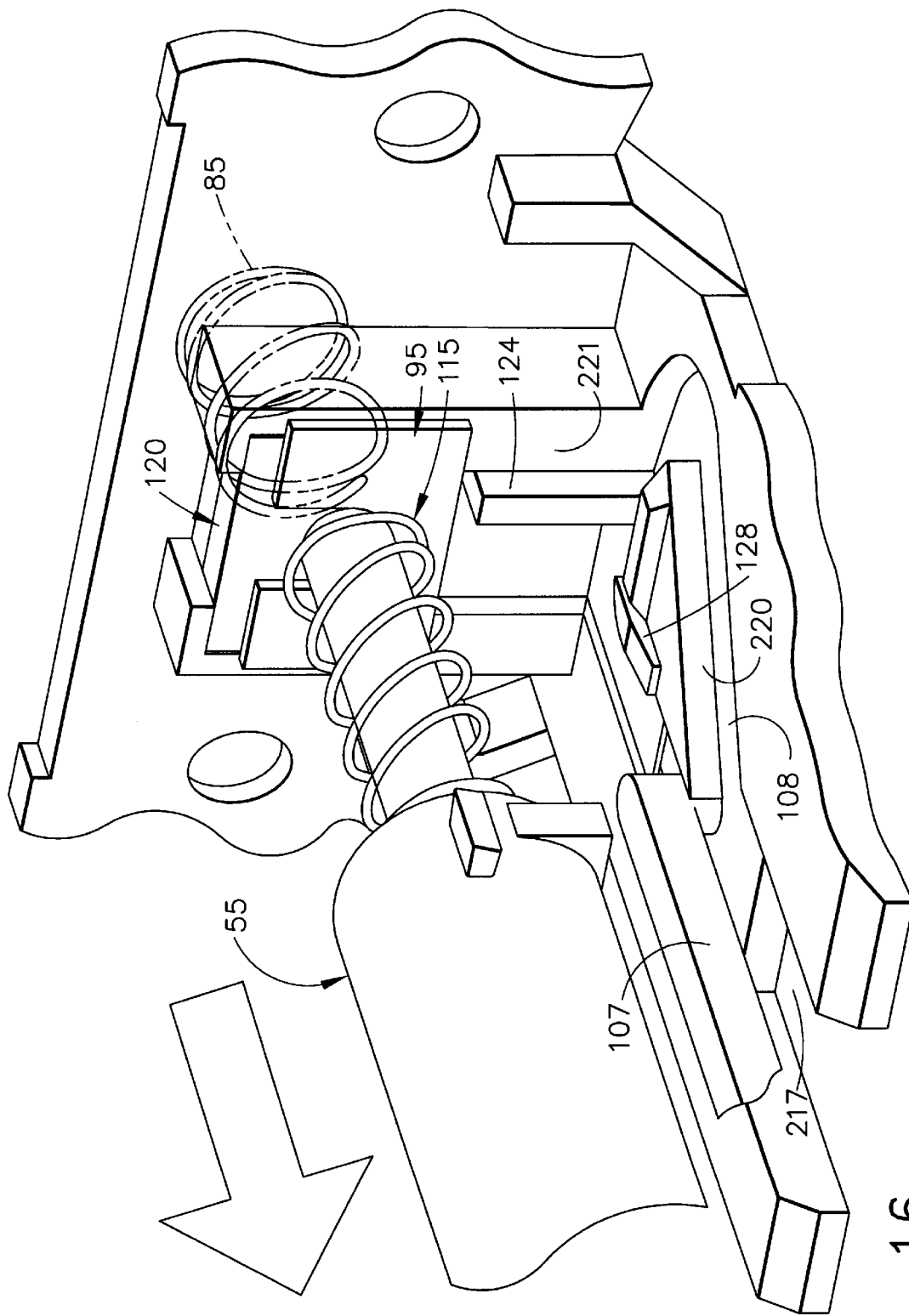
FIG. 16 is a partial perspective cross sectional view of an obturator of the present invention wherein the obturator shaft and knife collar have moved distally to unlock the shield by enabling the locking pawl to disengage from the second contact surface of the knife collar, enter the longitudinal channel located in the latch plate of the latch, enabling the shield and locking pawl to rapidly deploy distally; the handle and latch are partially cut away and the precock lever is removed for clarity.
Figure 17:
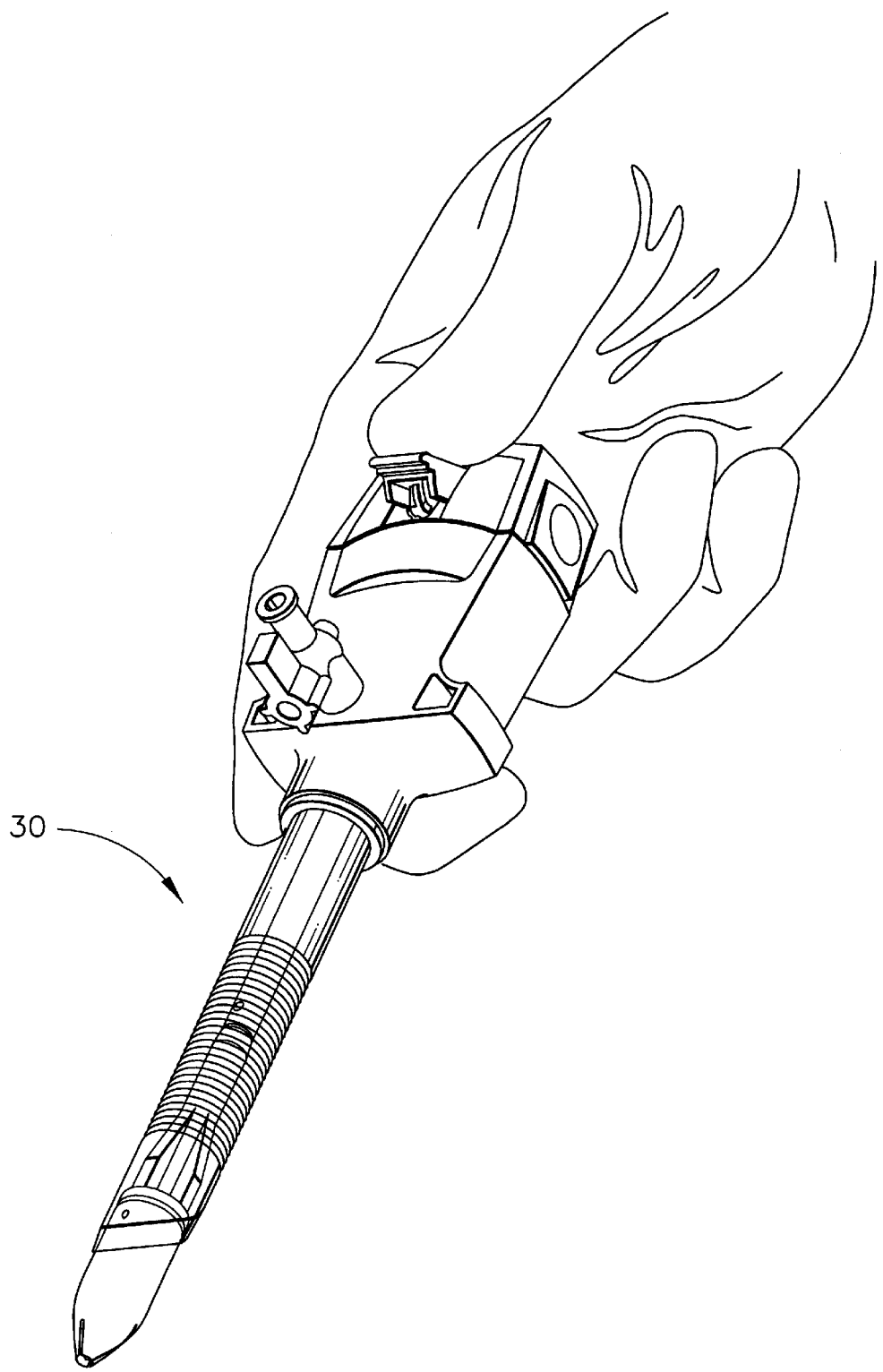
FIG. 17 is a perspective view of the trocar of the present invention with the surgeons thumb on the precock lever just prior to precocking the trocar.
Figure 18:
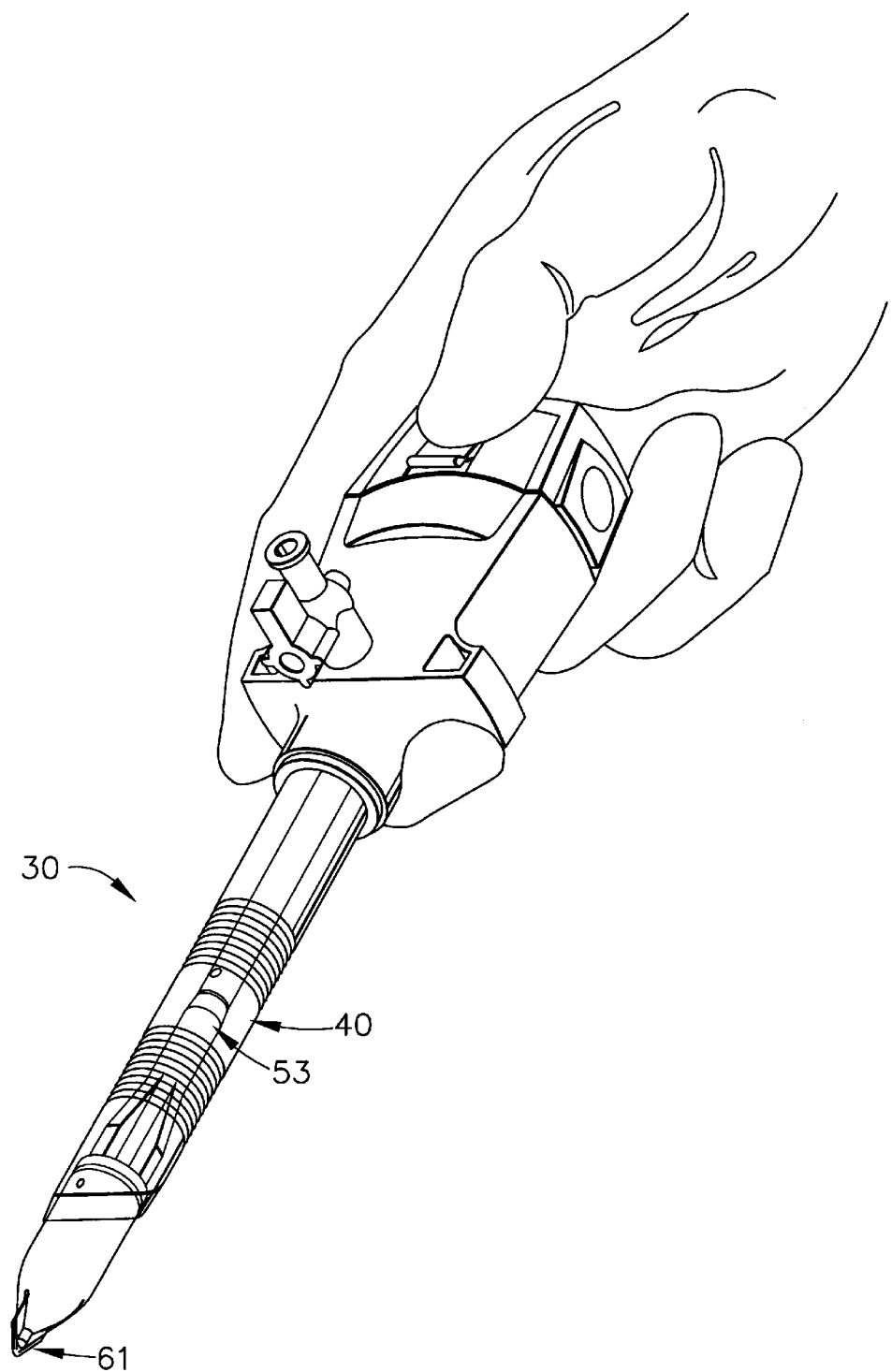
FIG. 18 is a perspective view of the precocked trocar of the present invention in the surgeons hand with the precock lever fully depressed, the shield fully retracted to expose the flat blade, and the shield deployment mechanism fully armed.

The shield deployment mechanism operates as follows (see FIGS. 15 and 16). Once the trocar 30 is precocked and the flat blade 61 is in contact with tissue, application of force on the obturator handle 51 displaces the obturator shaft assembly, comprising flat blade 61, the obturator shaft 60, and the knife collar 120, proximally against the distal biasing force of the knife spring 85. As described previously, the proximal stroke required to unlock the shield deployment mechanism is approximately 0.040 inches plus and minus 0.030 inches. As the knife collar 120 moves distally, the pawl 108 remains in contact with the distally moving pawl contact surface 124. When the knife collar 120 nears the proximal end of its stroke, surface 124 and pawl slot 130 move distally past the pawl 108 and the deflected arm 107 moves the pawl 108 in an arcuate path into contact with the pawl contact surface 128. At the end of the stroke, the pawl 108 is abutting the pawl contact surface 128, under bias from the deflected arm 107, and is holding the unlocked shield 55 in the retracted position ready to deploy. A reduction in tissue contact force on the flat blade 61 enables the biasing force from the knife spring 85 to displace, or stroke, the obturator shaft assembly distally. As the knife collar surface 128 is displaced distally, pawl 108 enters pawl slot 130 and the deflected arm 107 biases the pawl 108 into the longitudinal channel 217 in the latch plate 210. The pawl 108 is free to travel distally in channel 217 and the shield spring 115 rapidly biases the shield 55 distally to envelop the exposed flat blade 61. The precock lever 52 rotates outwardly, to the unactuated precock position, as the shield 55 moves distally. When the shield 55 nears its full deployment distally, the deflected shield locking arm 138 emerges from the cutout 106 on the tube member 100 and moves to the undeflected position, locking the shield 55 in the deployed, or extended position. To rearm the precock mechanism and re-expose the flat blade 61, the distal end of precock lever 52 is again depressed inwardly.

Figure 19:
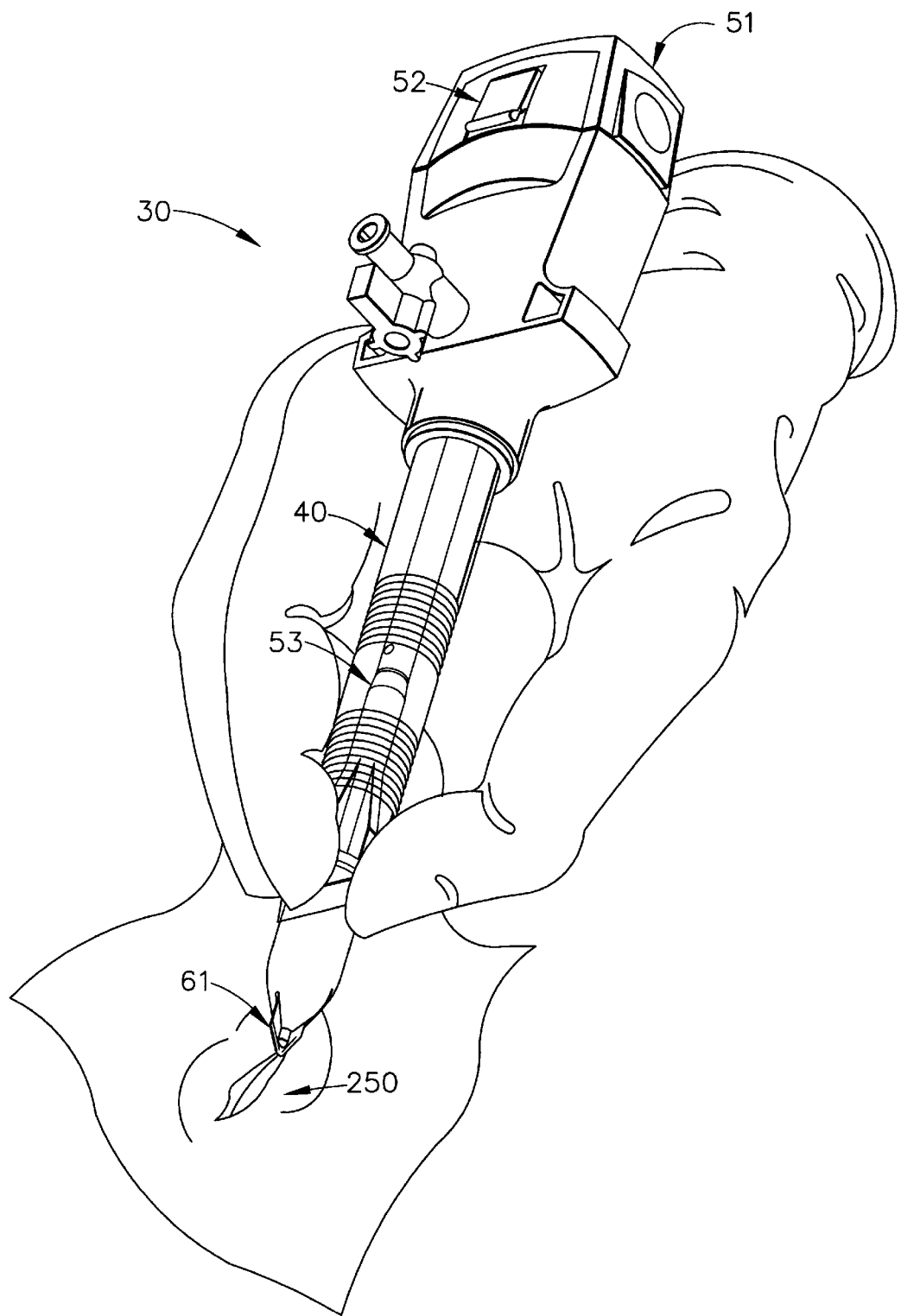
FIG. 19 is a perspective view of the precocked trocar of the present invention with the exposed flat blade being used as a scalpel to incise the skin of a patient prior to insertion of the trocar.

Referring to FIGS. 2, 3, and 19, the exposed flat blade 61 is unique as it can be used as a surgical scalpel to incise the exterior skin 250 of a patient (typically a mammal), or, as a penetrating tip for a surgical trocar 30. The flat bladed knife is superior to other trocar blade designs as it is ideally suited for both penetration and for making incisions. When the trocar 30 is used to make incisions, it is precocked, or armed, and the exposed blade is brought into contact with the exterior skin 250 of the patient. The angle that the longitudinal axis of the trocar 30 makes with the skin surface 250 can range between acute to obtuse, depending on surgeon preference. A distal force is applied to the obturator handle 51 or to the trocar cannula to make an incision. As the tissue is cut, resistance to penetration displaces, or strokes, the flat blade 61 proximally against the distal biasing force of the knife spring 85. When the force of penetration is less than the bias force applied by the knife spring 85, the proximal displacement of the flat blade 61 is less than the stroke or displacement required to unlock the shield locking mechanism and the operator can complete the incision without deploying the shield 55. When the force of penetration is greater than the bias force applied by the knife spring 85, the flat blade 61, the obturator shaft 60 and the knife collar 120 displaces proximally (full stroke) into the obturator 53, and the shield locking mechanism is unlocked. If the force of penetration is maintained, the flat blade 61 remains exposed and the incision can be completed. When the force of penetration is reduced on an unlocked shield 55, say at the end of an incision, the flat blade 61 moves distally under the biasing force of the knife spring 85, and the shield 55 rapidly deploys, or slides, distally to the extended position to envelop the flat blade 61. Once the shield 55 is extended, the precock lever 52 is returned to the precock position, and is locked into position by the shield locking arm 138 in the handle 51.

When using an armed trocar to penetrate the skin, and underlying fat, muscle, and fascia into the underlying cavity or joint, the extended flat blade 61 is placed in contact with the exterior skin surface of a patient, or in the incision described above. The longitudinal axis of the trocar 30 is generally perpendicular to the surface of the skin, although the axis can be angled at acute or obtuse angles with the skin surface 250. A proximal penetrating force applied to the obturator handle 51 moves, or strokes, the flat blade 61, the obturator shaft 60, and the knife collar 120 distally against the biasing force of the knife spring 85. When the penetrating force is greater than the knife spring biasing force, the flat blade 61 moves proximally through its full stroke, and unlocks the shield locking mechanism. Once the distal tip of the trocar 30 penetrates into the body cavity, the knife spring 85 biases the flat blade 61 proximally, and the shield 55 deploys, or slides, distally to an extended, locked position to envelop the flat blade 61. The precock lever 52 returns to its unactivated position.

The position of the precock lever 52 indicates whether the trocar 30 is in an armed condition. When the shield 55 is in the fully deployed or extended position, the distal end of precock lever 52 is in a fully extended position, with respect to the handle 51, as shown in FIG. 1. In FIG. 2, the trocar 30, is shown in the precocked, or armed, condition wherein the flat blade 61 is exposed, and the precock lever 52 is in an intermediate or partially extended position with respect to the handle 51.

The trocar obturator 53 is removable from the cannula assembly 40 by inwardly displacing the finger pads 204 into the obturator handle 51, thereby releasing the tab members 205 from cavities 44. Simultaneously, a proximal or pulling motion is applied to the handle 51 of the trocar obturator 50 causing the obturator 50 and the shield 55 to slide out of the trocar cannula 40.

The trocar 30 of the present design is constructed of conventional materials having the requisite biocompatability and mechanical requirements. The trocar obturator 50 may be typically manufactured from conventional materials including polymers such as polycarbonate, metals such as stainless steel, ceramics, polyetherimide, and conventional biocompatable materials and equivalents thereof. The piercing tip may be constructed from conventional materials including biocompatable metals such as stainless steel, ceramics, plastics, and the like. The trocar cannula 40 and the obturator handle 51 and the shield 55 as well as the locking arm 138 are preferably molded from conventional materials including biocompatible polymers such as polycarbonate, polyether-imide, silicone rubbers, and the like. The molded components are molded using conventional molding equipment utilizing conventional processes.

The present embodiment of the trocar 30, is a surgical trocar consisting of a cannula 40 and an obturator 53 with a flat blade 61 that can be exposed and used as a surgical scalpel. In another embodiment, the trocar 30, can be supplied to the surgeon as a component in a surgical kit. The kit should contain at least one trocar 30, of the present embodiment, in combination with other surgical devices such as trocars of various sizes, clip appliers, endocutters, sutures, needles, and the like. Also, in yet another embodiment, the preferred invention can be used in a kit consisting of a single obturator 53 of size, used with one or more cannulas 30 of like size, and with or without other surgical instrumentation.

The preferred invention is the combination of a shielded trocar with an exposable blade that can be used as a scalpel blade, or as a penetrating trocar blade. While a flat blade with generally planar surfaces is described, it is to be understood that a variety of blade shapes can be made that are equivalent. In one embodiment, if a blade is constructed that is generally triangular in cross section, with two long sides and one short side, a cutting surface can be added to the acute angle and can be made to perform in a like manner to a flat parallel blade. The long sides can be flat or arcuate and still meet the design intent. In an additional embodiment, three (or more) blades can be equally spaced about the longitudinal axis to form a blade shape that is a tri star in cross section. By adding a cutting surface to one or more of the blades, the non-flat blade can be used as a scalpel for incisions. The blades not selected for the incision are safely angled away from, or parallel to, the tissue at the incision site. Additionally, in another variation, one or more flat blades can be stacked up in parallel to produce an equivalent cutting blade. In yet another embodiment, a cutting blade, or tip, can be a portion of, or combined with, the obturator shaft. While many more equivalent blade embodiments exist, it should be obvious to one skilled in the art that a variety of tip or blade shapes can be constructed that meet design intent of the preferred embodiment of the trocar.

Trocars have been conventionally used to provide access to a surgical site in a patients body cavity or joint. A trocar is typically inserted by initially incising the skin 250 of the patient with a scalpel or other cutting blade and pressing the distal end of the trocar into the incision. The insertion site is selected by the surgeon to provide optimal access to the target surgical site within the body cavity. Sufficient force is applied to the trocar obturator handle in a direction along the longitudinal axis of the trocar so the piercing tip, or flat blade, of the trocar obturator effectively penetrates the patients skin, underlying fat tissue, muscle, and fascia. The distal end of the trocar obturator is then located by the surgeon to a position effective for access to the target surgical site. Then the trocar obturator assembly is removed from the trocar cannula by applying a rearward force to the trocar obturator handle. The trocar cannula is then used as a passageway to and from the patients body cavity.

The endoscopic surgical method of the present invention may be practiced using the trocar, shown in FIGS. 17–22, which generally consist of the trocar 30, the cannula 40, the trocar obturator 53, and the flat blade 61. The surgical method initially involves the preparation of the patient for endoscopic surgery, in a conventional manner, e.g., introduction of a pneumoperitoneum, use of the obturator flat blade 61 to make at least one incision in the skin 250 of a patient for each access site, and insertion of at least one trocar 30 of the present invention into the body cavity of the patient at the access site, using conventional endoscopic surgical techniques. Conventional endoscopic techniques are disclosed in the *Textbook of Laparoscopy*, Jaraoslav F. Hulka, M.D., Grune and Stratton, INC., New York (1985), and in *Laparoscopy for Surgeons*, Barry A. Salky, M.D., IGAKU-SHOIN Medical publishers, New York (1990). The trocar obturator 53 is then removed from the cannula 40, and the trocar cannula is available as a passageway to and from the body cavity. When using the trocar cannula in an endoscopic procedure, such as trocar cannula 40, the trocar handle 51 is typically disposed exterior to the body cavity wall while the distal end of the cannula tube 41 is within the body cavity. Various conventional endoscopic surgical instruments, surgical staplers, surgical clip appliers, sutures, needles, pharmaceuticals, tissue, tissue samples, drug delivery systems, electrosurgical devices, electrodes, suction irrigation devices, etc. are inserted through the trocar cannula 40 and maneuvered to the target surgical site where conventional endoscopic surgical techniques are utilized.

The following examples are illustrative of the principles and practices of the present invention.

EXAMPLE 1

A patient of conventional size and weight was prepared for surgery using conventional techniques including depilation of the epidermis in the region of expected incision, scrubbing, and rinsing with conventional fluids, and application of a conventional iodine solution. The patient was placed in a reclining position on a conventional operating table and covered with a sterile drape. The patient was anesthetized with a sufficient dose of conventional anesthetic effective to introduce an anesthetized state.

The patient was cannulated with an endotracheal tube and connected to a conventional anesthesia machine and ventilated as required. The abdominal cavity of the patient was insufflated in a conventional manner with carbon dioxide and five cannulas were inserted into the abdominal cavity with one trocar obturator of the present embodiment. For each surgical site, a cannula 40 was assembled with the obturator 53 to form trocar 30 and the precock lever 52 was activated to expose the flat blade 61 (see FIG. 18).

The exposed flat blade 61 of the preferred trocar embodiment was used as a surgical scalpel to incise the surgical site prior to insertion of the trocar 30. The blade 61 was exposed by depressing the precock lever inwardly to retract the shield (see FIG. 18). For some of the incisions using the flat blade 61, the surgeon used a light touch such that the skin of the patient was incised without deflecting the flat blade 61 proximally, into the obturator 53, and activating the shield deployment mechanism. The surgeon was able to accomplish the incision with one or more strokes of the flat blade 61 (see, for example, FIG. 19). For other incisions, it was the surgeons preference to apply a firmer proximal force to the exposed cutting blade of the trocar 30 during the cutting stroke such that the shield deployment mechanism is actuated. For this method, the surgeon placed the exposed knife blade 61 onto the skin 250 at the surgical site and applied a firmer distal force to the trocar 30 at the onset of the incision. The flat blade 61 moved proximal (full stroke), with respect to the handle 51, and the shield deployment mechanism was armed. The shield 55 remained retracted and the knife blade exposed for cutting until the surgeon reduced the distal incision force such that the knife spring 85 biased the flat blade 61 a small amount distally and initiated the shield 55 deployment. Once initiated, the shield 55 was rapidly deployed or snapped distally, with respect to the trocar 30, by the shield spring 115. When the surgeon removed the trocar 30 from the patient, the flat blade 61 was shielded reducing possible nicks or cuts from an exposed sharp. For additional incisions, the trocar 30 was recocked to expose the blade.

Figure 20:
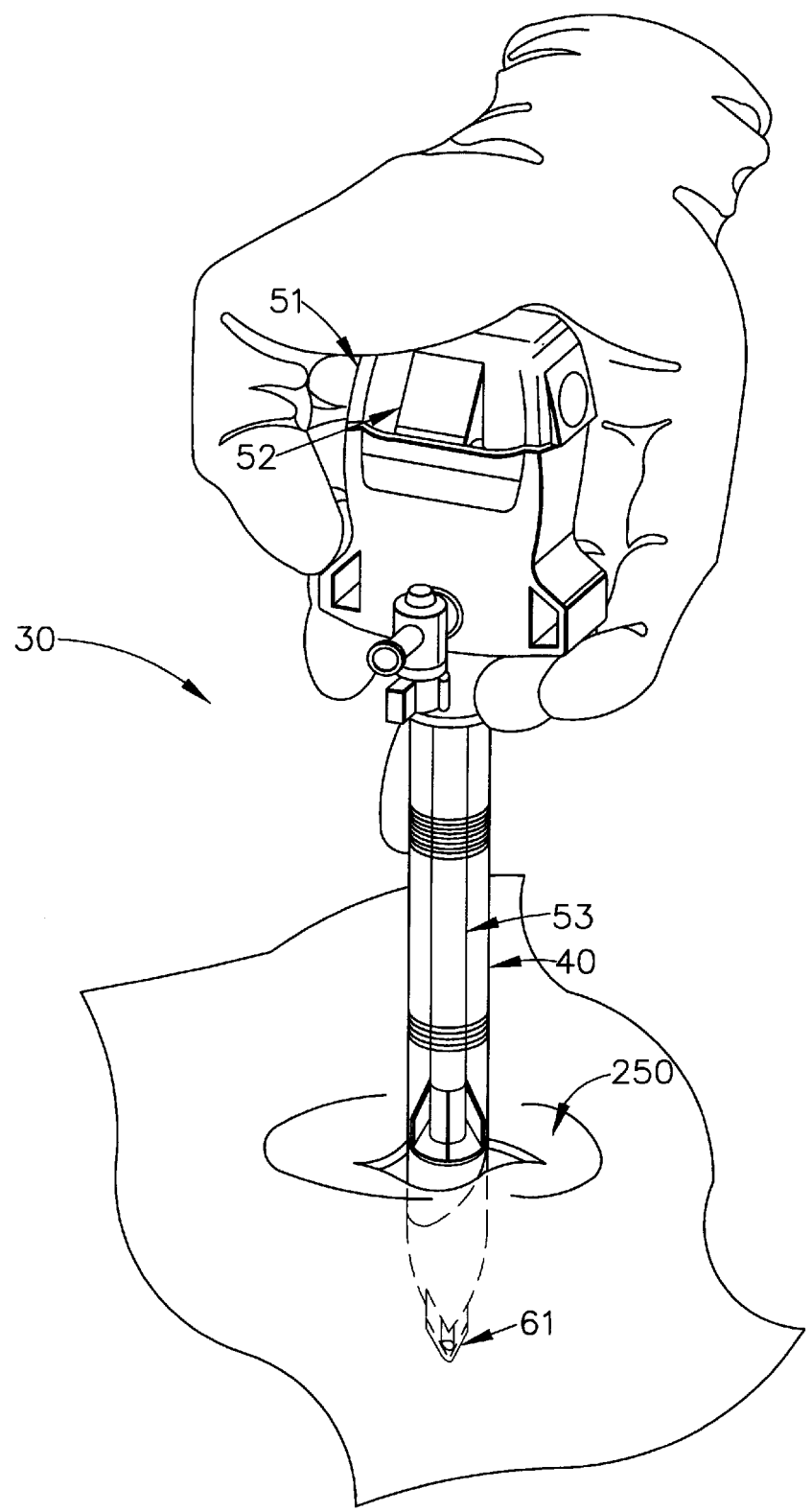
FIG. 20 is a perspective view of the trocar of the present invention immediately after insertion wherein the exposed flat blade is being used to penetrate into the tissue of a patient with the shield in a retracted position
Figure 21:
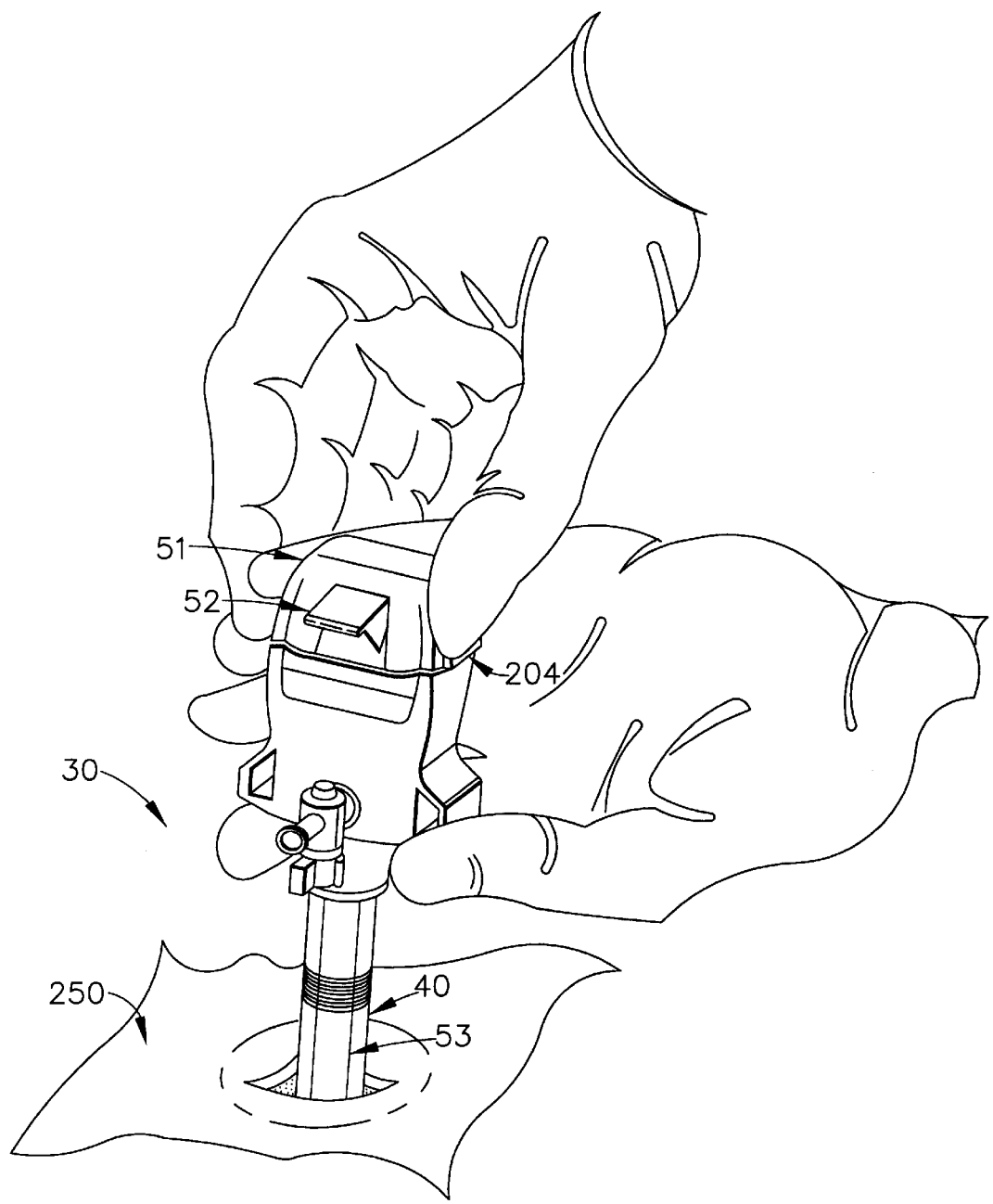
FIG. 21 is a perspective view of the trocar of the present invention after insertion into a body cavity with the surgeon unlocking the obturator from the cannula prior to removal of the obturator.
Figure 22:
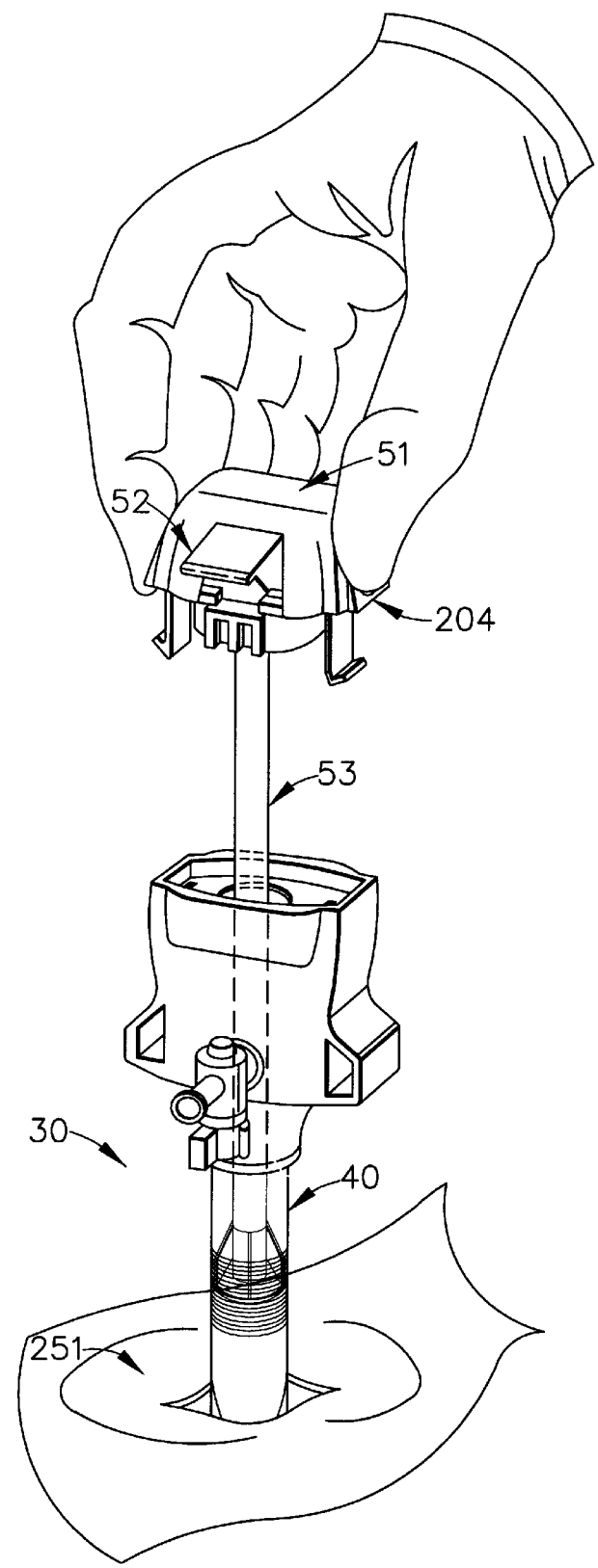
FIG. 22 is a perspective view of the trocar of the present invention after insertion into a body cavity with the surgeon removing the obturator from the cannula prior to endoscopic or arthroscopic surgery.

Once the incisions were made, the exposed flat blade 61 of the trocar 30 was placed within the incision at the surgical site, and the surgeon applied a distal force to initiate the penetration into the body cavity (see FIGS. 20 and 21). The penetration force moved the flat blade proximally (full stroke) with respect to the trocar handle 51, armed the shield deployment mechanism and then moved distally with the trocar 30 toward and into the body 251. Upon entry into the body cavity 251, the shield 55 of each trocar was deployed or snapped forward by shield spring 115. The shields were locked into an extended position enveloping the flat blade 61 of each trocar 30 thereby reducing the possibility of inadvertent piercing of internal organs, tissue, or blood vessels. Then the obturator assembly 53 was removed so that the trocar cannulas 40 remained in the abdominal cavity as pathways (see FIG. 22). An endoscope was inserted through one of the trocar cannulas 40. The endoscope was connected to a video monitor.

EXAMPLE 2

A human patient is prepared for surgery using conventional preparatory techniques and is effectively anesthetized using a sufficient dose of a conventional anesthetic. The patient is connected to conventional anesthesiology equipment, and as needed, ventilation equipment. After using conventional endoscopic preparatory practices, including insulation, and insertion of an endoscope, three trocars 30 of the present invention are inserted into the abdominal cavity of the patient by pressing the distal end of each trocar 30 into the exterior skin of the patient in the proximity of the target surgical sites. Prior to insertion, the trocars are precocked to expose the flat blade 61 by depressing the distal end of precock lever 52 inwardly into the obturator handle 51. Sufficient force is exerted by the surgeon on the trocar obturator handle 52, to arm the shield deployment mechanism, and cause the exposed flat blade 61 (along with shield 55) to pierce the patients skin and underlying fat, muscle tissue, and fascia. Optionally, the surgeon may use the flat blade 61 to make an incision. Then, the end of the trocar is brought into a position in the body cavity which is in the proximity of the surgical site. As the flat blade penetrates the abdominal wall, the flat blade 61 moves slightly distally and releases the shield deployment mechanism. The shield spring 115 deploys or snaps the shield distally to envelop the flat blade 61 where it is locked into place by the shield locking mechanism. The trocar obturator assembly 53 is then removed from the trocar cannula 40 and the shield 55 remains in a locked extended position covering the flat blade 61. An incision is made in the target site using a conventional endoscopic cutting instrument inserted through a cannula 40 and a piece of tissue is removed by grasping the tissue with a conventional endoscopic grasper and extracting the tissue trough another cannula 40. The trocar cannula 40 is made from a transparent material thereby enabling the surgeon to observe the tissue as it is guided through and out of the cannula 40.

The surgeon then inserts an endoscopic surgical needle and suture, using a conventional endoscopic needle holder, through a trocar cannula 40. The surgeon sutures the incision at the target surgical site, using conventional endoscopic techniques, and, removes the surgical needle and excess suture through the trocar cannula 40. Next the trocar cannulas 40 are removed from the patient. Finally, the trocar insertion sites are closed by conventional taping, suturing, and or stapling techniques.

There are many advantages of the flat bladed trocar of the present invention. The flat blade 61 can be easily exposed for use as a scalpel for incisions, or as a penetrating tip during trocar insertion. The ability of the trocar to be used as a scalpel offers added safety and reduced cost. The ability to use the trocar as the scalpel eliminates the need for the surgeon and operating room personnel to pass exposed sharps or scalpels back and forth, while making multiple surgical access site incisions. This reduces the risk of nicks or cuts through surgical gloves caused by contact with the exposed sharps, and, reduces the potential passage of communicable diseases from blood or other bodily fluids. In the cost conscious world of medicine today, the use of this preferred invention negates the need for scalpels during endoscopic surgery, and thus can reduce the cost of the surgical procedure.

Additionally, the surgeon has the ability to use the exposed knife as a scalpel in several modes. The exposed blade on a precocked trocar offers superior visibility when applying the trocar to a surgical site to penetrate the body cavity. Conventional trocars, without a precocking shield, apply the blunt shield to the surgical site. The diameter of the shield tip tends to obscure the insertion area. With the exposed blade of the trocar in the precocked condition, the surgeon can observe the contact of the point of the blade with the skin and know the exact site of penetration. Also, the surgeon can apply the flat blade 61 to skin with a higher distal force during the incision, arm the shield deployment mechanism, so that the shield will deploy and envelop the flat blade 61 as it is being withdrawn from the tissue. This automatically shields the exposed flat blade 61 upon withdrawal from the incision and reduces possible nicks or cuts from the flat blade, a feature that is not offered with conventional scalpels or trocars. The obturator is also unique as it can be used as a scalpel, without the cannula. This feature enables the surgeon to install as many cannulas as needed for the procedure and still retain the use of the obturator as a shielded scalpel for other uses such as tissue incisions, suture cutting, tape cutting and the like.

The precock lever 52 can be easily actuated with one hand to expose the flat blade 61. That is, a surgeon can precock the trocar by grasping the trocar 30 in one hand and depressing the distal end of the precock lever 52 with the thumb or a finger on that hand. Additionally, the precock lever position provides a visual or tactile indicator as to the status of the trocar, precocked with an exposed blade, or uncocked with a locked shield deployed over the blade. A further advantage is the shield mechanism is actuated by a proximal and distal motion of the flat blade 61, with respect to the trocar obturator 53 and may be more sensitive than a mechanism actuated solely by shield movement.

Although this invention has been shown and described with respect to detailed embodiments thereof, it will be understood by those skilled in the art that various changes in form and detail thereof may be made without departing from the spirit and the scope of the claimed invention. For example, although a pivoting lever is specifically illustrated for retracting the shield to expose the obturator blade, the lever can simply be any projecting piece which is capable of facilitating the engagement of the shield, such as a conventional slider mechanism. Additionally, different mechanisms for locking the shield in its retracted position, releasing the locking mechanism from preventing axial movement of the shield, and deploying the shield from its retracted to extended positions, are well within the scope of the invention.

What is claimed is:

1. A method for establishing a surgical port for an internal body cavity during endoscopic or arthroscopic surgery on a patient, said method comprising:
   a) providing a trocar having an obturator assembly and a cannula assembly surrounding said obturator assembly, said obturator assembly capable of being inserted into and withdrawn from said cannula assembly, said obturator assembly having:
      i) an obturator, said obturator including a flat cutting blade at a distal end of said obturator, said flat cutting blade having first and second planar surfaces generally parallel to each other, said planar surfaces converging to a cutting edge surface, and a handle at a proximal end of said obturator;
      ii) a shield slidably mounted on said obturator, said shield movable from a precocked position wherein said shield is retracted so as to expose said flat cutting blade of said obturator, to an extended position wherein said shield covers said flat cutting blade, said shield having a shield retaining surface thereon and a precock surface thereon;
      iii) a precock lever movable from an unactuated position wherein said shield is in the extended position to an actuated position wherein said shield is in the precocked position, said precock lever having a shield retraction surface cooperable with said precock surface of said shield for moving said shield from the extended position to the precocked position when said precock lever is moved from the unactuated position to the actuated position; and
      iv) a shield retaining subassembly cooperable with said shield retaining surface of said shield, said shield retaining subassembly adapted to hold said shield in the precocked position when said precock lever has been moved from the unactuated position to the actuated position;
   b) moving the precock lever from the unactuated position to the actuated position so as to expose said flat cutting blade of said obturator upon retraction of said shield from its extended position to its precock position;
   c) incising the skin of the patient with said exposed flat cutting blade of said obturator;
   d) applying a penetrating force against the incised skin with said exposed flat cutting blade of said obturator so as to gain entry of said trocar into the internal body cavity of the patient; and
   e) removing said obturator assembly from said cannula assembly so as to provide the surgical port through the cannula assembly into the internal body cavity of the patient.

2. The method of claim 1 wherein said obturator is movable axially relative to said handle, said obturator is biased in the distal direction, and said obturator assembly has a shield deployment mechanism cooperable with said shield retaining subassembly, said shield deployment mechanism releasing said shield retaining subassembly from said shield retaining surface of said shield so as to allow movement of said shield from the precock position to the extended position when said obturator is moved proximally over an unlocking proximal distance.

3. The method of claim 2 wherein when the skin of the patient is incised, the proximal movement of said obturator does not exceed the unlocking proximal distance, said shield deployment mechanism is not released, and said flat cutting blade remains exposed with said shield in the prococked position.

4. The method of claim 2 wherein the skin of the patient is incised, the proximal movement of said obturator equals or exceeds the unlocking proximal distance, said shield deployment mechanism is released, and said shield moves from its precock position to is extended position so as to cover said flat cutting blade of said obturator.

* * * * *